(12) United States Patent
Wang et al.

(10) Patent No.: US 8,859,616 B2
(45) Date of Patent: Oct. 14, 2014

(54) COMPOUNDS AND METHODS FOR ENHANCING HAIR GROWTH

(75) Inventors: Jenny W. Wang, Irvine, CA (US); David F. Woodward, Lake Forest, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/354,479

(22) Filed: Jan. 20, 2012

(65) Prior Publication Data

US 2012/0190733 A1    Jul. 26, 2012

Related U.S. Application Data

(60) Provisional application No. 61/435,126, filed on Jan. 21, 2011.

(51) Int. Cl.
| | | |
|---|---|---|
| *A01N 43/08* | (2006.01) | |
| *A61K 31/215* | (2006.01) | |
| *A61K 31/5575* | (2006.01) | |
| *A61K 8/46* | (2006.01) | |
| *A61Q 7/00* | (2006.01) | |
| *A61K 31/575* | (2006.01) | |

(52) U.S. Cl.
CPC .............. *A61K 31/5575* (2013.01); *A61K 8/46* (2013.01); *A61Q 7/00* (2013.01); *A61K 31/575* (2013.01)
USPC ........... 514/468; 514/438; 514/443; 514/449; 514/461; 514/469; 514/529; 514/546; 514/553; 514/557; 514/568

(58) Field of Classification Search
USPC ......... 514/275, 438, 443, 449, 461, 468, 469, 514/506, 510, 529, 546, 553, 557, 568, 569
See application file for complete search history.

(56) References Cited

U.S. PATENT DOCUMENTS

| | | |
|---|---|---|
| 3,382,247 A | 5/1968 | Anthony et al. |
| 3,644,363 A | 2/1972 | Kim |
| 4,128,577 A | 12/1978 | Nelson |
| 4,139,619 A | 2/1979 | Chidsey |
| 4,311,707 A | 1/1982 | Birnbaum et al. |
| 4,543,353 A | 9/1985 | Faustini et al. |
| 4,596,812 A | 6/1986 | Chidsey et al. |
| 4,599,353 A | 7/1986 | Bito |
| 4,812,457 A | 3/1989 | Narumiya et al. |
| 4,839,342 A | 6/1989 | Kaswan |
| 4,883,581 A | 11/1989 | Dickakian |
| 4,888,354 A | 12/1989 | Chang et al. |
| 4,889,845 A | 12/1989 | Ritter et al. |
| 4,952,581 A | 8/1990 | Bito et al. |
| 4,968,812 A | 11/1990 | Wang |
| 5,001,153 A | 3/1991 | Ueno et al. |
| 5,194,429 A | 3/1993 | Ueno et al. |
| 5,280,018 A | 1/1994 | Ritter et al. |
| 5,288,754 A | 2/1994 | Woodward et al. |
| 5,296,504 A | 3/1994 | Stjernschantz et al. |
| 5,321,128 A | 6/1994 | Stjernschantz et al. |
| 5,352,708 A | 10/1994 | Woodward et al. |
| 5,422,368 A | 6/1995 | Stjernschantz et al. |
| 5,422,369 A | 6/1995 | Stjernschantz et al. |
| 5,431,881 A | 7/1995 | Palacios |
| 5,474,979 A | 12/1995 | Ding et al. |
| 5,480,900 A | 1/1996 | DeSantis et al. |
| 5,508,303 A | 4/1996 | Isogaya et al. |
| 5,510,383 A | 4/1996 | Bishop et al. |
| 5,545,655 A | 8/1996 | Friedlander et al. |
| 5,578,618 A | 11/1996 | Stjernschantz et al. |
| 5,578,643 A | 11/1996 | Hanson et al. |
| 5,607,978 A | 3/1997 | Woodward et al. |
| 5,688,819 A | 11/1997 | Woodward |
| 5,698,733 A | 12/1997 | Hellberg et al. |
| 5,773,472 A | 6/1998 | Stjernschantz et al. |
| 6,025,392 A | 2/2000 | Selliah et al. |

(Continued)

FOREIGN PATENT DOCUMENTS

| | | |
|---|---|---|
| CA | 1208560 | 7/1986 |
| CA | 2144967 | 3/1994 |

(Continued)

OTHER PUBLICATIONS

Maruyama et al., "Design and synthesis of a highly selective EP4-receptor agonist. Part 1: 3,7-dithiaPG derivatives with high selectivity", Aug. 6, 2001, Bioorganic & Medicinal Chemistry Letters, vol. 11, Issue 15, pp. 2029-2031.*

Maruyama et al., "Design and synthesis of a highly selective EP4-receptor agonist. Part 2: 5-thia and 9β-haloPG derivatives with improved stability", Aug. 6, 2001, Bioorganic & Medicinal Chemisty Letters, vol. 11, Issue 15, pp. 2033-2035.*

Maruyama et al., "Design and synthesis of a selective EP4-Receptor agonist. Part 1: discovery of 3,7-DithiaPGE1 derivatives and identification of Their ω chains", Apr. 2002, Bioorganic & Medicinal Chemistry, vol. 10, Issue 4, pp. 975-988.*

Maruyama et al., "Design and Synthesis of a Selective EP4-Receptor Agonist. Part 2: 3,7-DithiaPGE1 Derivatives with High Selectivity", Apr. 2002, Bioorganic & Medicinal Chemistry, vol. 10, Issue 4, pp. 989-1008.*

Maruyama et al., "Design and synthesis of a selective EP4-receptor agonist. Part 3: 16-phenyl-5-thiaPGE1 and 9-β-halo derivatives with improved stability", Jun. 2002, Bioorganic & Medicinal Chemistry, vol. 10, Issue 6, pp. 1743-1759.*

(Continued)

*Primary Examiner* — My-Chau T Tran
(74) *Attorney, Agent, or Firm* — Mark D. Kafka

(57) ABSTRACT

The present invention provides a method for stimulating hair growth in a mammalian species or converting vellus hair or intermediate hair to terminal hair or stimulating hair follicles to increase hair growth and one or more properties selected from the group consisting of luster, sheen, brilliance, gloss, glow, shine or patina of hair associated with the follicles or increasing one or more of: length, thickness, number, and density, of eyelash hair or eyebrow hair comprising applying to the skin of a patient a composition comprising an effective amount of an $EP_3$ agonist or an $EP_4$ agonist prodrug or a mixture thereof. Such compositions which are used in treating the skin or scalp of a human or non-human animal may comprise an effective amount of 3, 7 or 3 and 7 thia prostanoic acid. A mixture of 3,7-dithia PGE1 and 3,7-dithia PGE1-isopropyl ester is preferred for this treatment.

20 Claims, No Drawings

(56) References Cited

U.S. PATENT DOCUMENTS

| | | | |
|---|---|---|---|
| 6,124,344 | A | 9/2000 | Burk |
| 6,160,129 | A | 12/2000 | Burk |
| 6,232,344 | B1 | 5/2001 | Feng et al. |
| 6,254,860 | B1 | 7/2001 | Garst |
| 6,258,844 | B1 | 7/2001 | Garst et al. |
| 6,262,105 | B1 | 7/2001 | Johnstone |
| 6,350,442 | B2 | 2/2002 | Garst |
| 6,403,649 | B1 | 6/2002 | Woodward |
| 6,410,591 | B1 | 6/2002 | Burk |
| 6,441,047 | B2 | 8/2002 | DeSantis |
| 6,538,018 | B1 | 3/2003 | Burk |
| 6,767,920 | B2 | 7/2004 | Burk |
| 6,956,057 | B2 | 10/2005 | Woodward |
| 7,351,404 | B2 * | 4/2008 | Woodward et al. .......... 424/70.1 |
| 7,368,436 | B2 | 5/2008 | Gleave et al. |
| 7,388,029 | B2 | 6/2008 | DeLong et al. |
| 7,705,041 | B2 * | 4/2010 | Michelet et al. ............. 514/461 |
| 7,713,968 | B2 * | 5/2010 | Donde et al. ............... 514/231.5 |
| 8,038,988 | B2 | 10/2011 | Woodward et al. |
| 8,101,161 | B2 * | 1/2012 | Woodward et al. .......... 424/70.1 |
| 2002/0044953 | A1 | 4/2002 | Michelet et al. |
| 2002/0103255 | A1 | 8/2002 | Hellberg et al. |
| 2002/0172693 | A1 | 11/2002 | DeLong et al. |
| 2003/0083381 | A1 | 5/2003 | Kumagai et al. |
| 2003/0147823 | A1 | 8/2003 | Woodward et al. |
| 2003/0199590 | A1 | 10/2003 | Cagle et al. |
| 2004/0052760 | A1 | 3/2004 | Michelet et al. |
| 2005/0222232 | A1 | 10/2005 | Delong et al. |
| 2006/0121069 | A1 * | 6/2006 | DeLong et al. ............... 424/400 |
| 2007/0078175 | A1 | 4/2007 | Boulle et al. |
| 2009/0018204 | A1 | 1/2009 | Brinkenhoff |
| 2012/0295972 | A1 * | 11/2012 | Woodward et al. ........... 514/546 |
| 2012/0302588 | A1 * | 11/2012 | Woodward et al. ........... 514/275 |

FOREIGN PATENT DOCUMENTS

| | | |
|---|---|---|
| CA | 2174655 | 4/1995 |
| CA | 1339132 | 7/1997 |
| EP | 0170258 | 2/1986 |
| EP | 0249194 | 12/1987 |
| EP | 0308135 | 3/1989 |
| EP | 0639563 | 2/1995 |
| FR | 2239458 | 7/1973 |
| JP | S49-069636 | 7/1974 |
| JP | 61-218510 | 9/1986 |
| JP | H05-0331025 | 12/1993 |
| JP | H09-295921 | 11/1997 |
| JP | 10-287532 | 10/1998 |
| WO | 1998-033497 | 8/1979 |
| WO | 1989-003384 | 4/1989 |
| WO | 1995-011003 | 4/1995 |
| WO | 1997-031895 | 9/1997 |
| WO | 1999-012895 | 3/1999 |
| WO | 2000-054810 | 9/2000 |
| WO | 2001-074307 | 10/2001 |
| WO | 2001-074315 | 10/2001 |
| WO | 2009-011744 | 1/2009 |
| WO | 2012-068515 | 5/2012 |

OTHER PUBLICATIONS

Maruyama et al., "Design and synthesis of a selective EP4-receptor agonist. Part 4: practical synthesis and biological evaluation of a novel highly selective EP4-receptor agonist", Jul. 2002, Bioorganic & Medicinal Chemistry, vol. 10, Issue 7, pp. 2103-2110.*

Woodward et al., "Prostanoid EP4 Receptor Stimulation Produces Ocular Hypotension by a Mechanism That Does Not Appear to Involve Uveoscleral Outflow", Jul. 2009, Investigative Ophthalmology & Visual Science, vol. 50, No. 7, pp. 3320-3328.*

Abramovitz, Mark et al, The Utilization of Recombinant prostanoid Receptors to Determine the Affinities and Selectivities of Prostaglandins and Related Analogs, Biochimica et Biophysica Acta, 2000, 285-293, 1483.

Abramovitz, Mark, Cloning and Expressing of a cDNA for the Human prostanoid FP Receptor, Journal of Biological Chemistry, 1994, 2632-2636, 269(4).

Adis Data Information, ZD 6416, 2003.

ADIS, Alprostadil (NexMed) Alprox-TDTM, BefarTM, FemproxTM, Prostaglandin E1 (NewMed), Adis R & D Profile, 1999, 413-414, 2(6), Adis International Limited.

Al-Sereiti, M.R., Pharmacology of Rosemary (Rosmarinus Officinalis Linn.) and its Therapeutic Potentials, Indian Journal of Experimental Biology, 1999, 124-130, 37.

Allenby, A.C. et al, Mechanism of Action of Acclerants on Skin Penetration, Br. J. Derm, 1969, 47-55, 81(Supp. 4).

Allergan Clinical Study Report, 192024-008, 2000.

Allergan, Inc., Dermatologic and Ophthalmic Drugs Advisory Committee Briefing Document for Bimatoprost Solution 0.03%, Dermatologic and Ophthalmic Drugs Advisory Committee Briefing Document for Bimatoprost Solution 0.03%, Oct. 29, 2008, 1-108.

Alm, Albert et al, Effects on Intraocular Pressure and Side Effects of 0.005% Latanoprost Applied Once Daily, Evening or Morning, Ophthalmology, 1995, 1743-1752, 102.

Alm, Albert et al, Phase III Latanoprost Studies in Scandinavia, the United Kingdom and the United States, Survey of Ophthalmology, Feb. 1997, S105-S110, 41(2).

Alm, Albert et al, Uveoscleral Outflow—A Review, Experimental Eye Research, 2009, 760-768, 88(4).

Alm, Albert, The Potential of Prostaglandin Derivates in Glaucoma Therapy, Current Opinion in Ophthalmology, 1993, 44-50, 4(11).

Audoly, Laurent et al, Identification of Specific EP Receptors Responsible for the Hemodynamic Effects of PGE2, Am. J. Physiol., 1999, H924-H930, 277.

Badawy, Sherif et al, Salt Selection for Pharmaceutical Compounds, Preformulation in Solid Dosage Form Development (Informa Healthcare), 2008, 63-80, Chapter 2.3, Adeyeyem, Moji, ed.

Bartmann, W., Synthesis and Biological Activity, Luteolytic Prostaglandins, Feb. 1979, 301-311, 17(2).

Bastin, Richard et al, Salt Selection and Optimisation Procedures for Pharmaceutical New Chemical Entities, Organic Process Research & Development, 2000, 427-435, 4.

Bean, Gerald, Commercially Available Prostaglandin Analogs for The Reduction of Intraocular Pressure: Similarities and Differences, Survey of Ophthalmology, 2008, S69-S84, 53 (Supp. 1).

Berge, Stephen M., Pharmaceutical Salts, Journal of Pharmaceutical Sciences, Jan. 1977, 1-19, 66 (1).

Berglund, Barbara et al, Investigation of Structural Analogs of Prostaglandin Amides for Binding to and Activation of CB1 and CB2 Cannabinoid Receptors in Rat Brain and Human Tonsils, Adv Exp Med Biol, 1999, 527-533, 469.

Bird, Katie, Nano Carriers Enhance Skin Penetration and Antioxidant Effect of CoQ10, Cosmetics design-asia.com, Apr. 8, 2010, 1 Page, William Reed Business Media SAS.

Bito, L.Z. et al, Long-Term Maintenance of Reduced Intraocular Pressure by Daily or Twice Daily Topical Application of Prostaglandins to Cat or Rhesus Monkey Eyes, Investigative Ophthalmology & Visual Science, 1983, 312-319, 24(3).

Bito, Laszlo, A new approach to the medical management of glaucoma, from the bench to the clinic, and beyond, Investigative Ophthalmology & Visual Science, 2001, 1126-1133, 42(6), The Proctor Lecture.

Brandt, James et al, Comparison of Once- or Twice-Daily Bimatoprost with Twice-Daily Timolol in Patients with Elevated IOP, American Academy of Ophthalmology, 2001, 1023-1031, 108(6).

Brandt, James, PA022 Phase III, 3-month Comparison in Timolol with AGN-192024: A New Ocular Hypotensive Lipid for Glaucoma Management, Presented at 2000 Am. Acad. Ophthalmology, Ann. Mtg., Oct. 23, 2000, 1 Page.

Brubaker, Richard et al, Effects of AGN 192024, a new Ocular Hypotensive Agent, on Aqueous Dynamics, American journal of Ophthalmology, 2001, 19-24, 131(1).

Bundy, Gordon, Synthesis of 17-Phenyl-18, 19, 20-Trinorprostaglandins I. The PG1 Series, Prostaglandins, 1975, 1-4, 9(1).

Business Wire, Phase III Lumigan, AGN-192024—Data Presented At American Academy of Ophthalmology, American Academy of Ophthalmology, 2000, 1-3, Retrieved Dec. 14, 2010.

(56) References Cited

OTHER PUBLICATIONS

Cadet, Patrick et al, Molecular Identification and Functional Expression of µ3, a Novel Alternatively Spliced Variant of the Human µ Opiate Receptor Gene, J. Immunol., 2003, 5118-5123, 170.

Camras, Carl B. et al, Bimatoprost, the Prodrug of a Prostaglandin Analogue, Br J Ophthalmol, 2008, 862-863, 92.

Camras, Carl B. et al, Comparison of Latanoprost and Timolol in Patients with Ocular Hypertension and Glaucoma, Ophthalmology, 1996, 138-147, 103(1).

Camras, Carl B. et al, Detection of the Free Acid of Bimatoprost in Aqueous Humor Samples From Human Eyes Treated with Bimatoprost Before Cataract Surgery, The American Academy of Ophthalmology, 2004, 2193-2198, 7pg, n/a, American Academy of Ophthalmology.

Camras, Carl B. et al, Latanoprost, a prostaglandin Analog, for Glaucoma Therapy, Ophthalmology, 1996, 1916-1924, 103(11).

Camras, Carl B. et al, Multiple Dosing of Prostaglandin F2α or Epinephrine on Cynomolgus Monkey Eyes, Investigative Ophthalmology & Visual Science, Sep. 1988, 1428-1436, 29(9).

Camras, Carl B. et al, Multiple Dosing of Prostaglandin F2α or Epinephrine on Cynomolgus Monkey Eyes, Investigative Ophthalmology & Visual Science, 1987, 463-469, 28(3).

Camras, Carl B. et al, Multiple Dosing of Prostaglandin F2α or Epinephrine on Cynomolgus Monkey Eyes, Investigative Ophthalmology & Visual Science, 1987, 921-926, 28(6).

Camras, Carl B. et al, Reduction of Intraocular Pressure in Normal and Glaucomatous Primate (Aotus Trivirgatus) Eyes by Topically Applied Prostaglandin F2α, Current Eye Research, 1981, 205-209, 1 (4).

Cantor, Louis et al, Levels of Bimatoprost Acid in the Aqueous Humour After Bimatoprost Treatment of Patients with Cataract, Br. J. Ophthalmol, 2007, 629-632, 91.

CAS RN 155206-00-1 May 20, 1994.

Cayatte, Antonio et al, The Thromboxane A2 Receptor Antagonist, S18886, Decreases atherosclerotic Lesions and serum Intracellular Adhesion Molecule-1 in the Apo E Knockout Mouse, 71st Scientific Sessions, 1998, I-115 (Abstract), 98(17).

Chen, June et al, AGN 191129: A Neutral Prostaglandin F2n (PGF2n) Analog That Lacks the Mitogenic and Uterotonic Effects Typical of FP Receptor Agonists, Glaucoma, Anatomy & Pathology, Physiology & Pharmacology, 1999, 3562-B420, 40(4).

Chen, June et al, Replacement of the Carboxylic Acid Group of Prostaglandin F2α (PGF2α) with Certain Non-Ionizable Substituents Results in Pharmacologically Unique Ocular Hypotensive Agents, 11th Intl Conf. Advances Prostaglandin & Leukotriene Res.: Basic Sci. & New Clinical Applications—Abstract Book, 2000, 1 page.

Chen, June et al, Studies on the Pharmacology of Prostamide F2α, A Naturally Occurring Substance, Brit. J. Pharmacology, 2001, 63P, 133.

Chyun, Yong et al, Stimulation of Bone Formation by Prostaglandin E2, Prostaglandins, 1984, 97-103, 27(1).

Clissold, D., The Potential for Prostaglandin Pharmaceuticals, Lipids in Health and Nutrition, 1999, 115-129, 244, The Royal Society of Chemistry.

Cohen, Joel, Enhancing the Growth of Natural Eyelashes: The Mechanism of Bimatoprost-Induced Eyelash Growth, Dermatol Surg, 2010, 1361-1371, 36(9).

Coleman, Robert et al, Prostanoids and Their Receptors, Comprehensive Medicinal Chemistry, 1990, 643-714, 3.

Coleman, Robert, VIII. International union of Pharmacology Classification of Prostanoid Receptors: Properties, Distribution, and Structure of the Receptors and Their Subtypes, The American Society for Pharmacology and Experimental Therapeutics, 1994, 205-229, 26(2).

Collins, Paul et al, Synthesis of Therapeutically Useful Prostaglandin and Prostacyclin Analogs, Chem. Rev., 1993, 1533-1564, 93.

Colombe, Laurent et al, Prostaglandin metabolism in human hair follicle, Experimental Dermatology, May 16, 2007, 762-769, 16, US.

Corsini, A. et al, (5Z)-Carbacyclin Discriminates Between Prostacyclin-Receptors Coupled to Adenylate Cyclase in Vascular Smooth Muscle and Platelets, Br. J. Pharmac., 1987, 255-261, 90.

Cox, Colin et al, Protein Fabrication Automation, Protein Science, 2007, 379-390, 16.

Crowston, Jonathan et al, Effect of Bimatoprost on Intraocular Pressure in prostaglandin FP Receptor Knockout Mice, Investigative Ophthalmology & Visual Science, 2005, 4571-4577, 46.

Davies, Sean, Hydrolysis of Bimatoprost (Lumigan) to Its Free Acid by Ocular Tissue in Vitro, Journal of Ocular Pharmacology and Therapeutics, 2003, 45-54, 19(1).

De Asua, L Jimenez et al, The Stimulation of the Initiation of DNA Synthesis and Cell Division in Swiss Mouse 3T3 Cells by Prostaglandin F2α Requires Specific Functional Groups in the Molecule, J. Biol. Chemistry, 1983, 8774-8780, 256(14).

Dean, T.R. et al, Improvement of Optic Nerve Head Blood Flow After One-Week Topical Treatment with Travoprost (AL06221) In The Rabbit, Investigative Ophthalmology & Visual Science, Mar. 15, 1999, 2688-B563, 40(4).

Del Toro, F. et al, Characterization of Prostaglandin E2 Receptors and Their Role in 24,25-(OH)2D3-Mediated Effects on Resting Zone Chondrocytes, Journal of Cellular Physiology, 2000, 196-208, 182.

Delong, Mitchell, Prostaglandin Receptor Ligands: Recent Patent Activity, IDrugs, 2000, 196-208, 3(9).

Depperman, William, Up-To-Date Scalp Tonic, Book Reviews, 1970, 1115, 283(20).

Dirks, Monte et al, Efficacy and Safety of the Ocular Hypotensive Lipid™ 192024 in Patients with Elevated IOP: A 30-Day Comparison with Latanoprost, Investigative Ophthalmology & Visual Science, Mar. 15, 2000, S514, 41(4).

Dubiner, Harvey, Efficacy and Safety of Bimatoprost in Patients With Elevated Intraocular Pressure: a 30-Day Comparison With Latanoprost, Surv. Ophthalmol, 2001, S353-S560, 45(4).

Easthope, Stephanie et al, Topical Bimatoprost, Drug Aging, 2002, 231-248, 19(3).

Eisenberg, Dan et al, A Preliminary Risk-Benefit Assessment of Latanoprost and Unoprostone in Open-Angle Glaucoma and Ocular Hypertension, Drug Safety, 1999, 505-514, 20(6).

Ellis, Cathy et al, Metabolism of Prostaglandin D2 in the Monkey*, The Journal of Biological Chemistry, 1979, 4152-4163, 254(10).

Emu Oil Hairloss and Frontal Regrowth, 2010, 4 Pages, www.hairloss-research.org/blog/?p=73.

Enyedi, Laura et al, The Effectiveness of Latanoprost for the Treatment of Pediatric Glaucoma, J AAPOS, 1999, 33-39, 3(1).

Ezure, T. et al, Involvement of Sonic Hedgehog in Cyclosporine A Induced Initiation of Hair Growth, Journal of Dermatological Science, 2007, 168-170, 47.

Fagot, Dominique et al, Mitogenic Signaling by Prostaglandins in Chemically Transformed Mouse Fibroblasts: Comparison with Phorbol Esters and Insulin, Endocrinology, 1993, 1729-1734, 132(4).

Fall, P.M., Inhibition of Collagen Synthesis by Prostaglandins in the Immortalized Rat Ostroblastic Cell Line Pyla: Structure-Activity Relations and Signals Transduction Mechanisms, J. Bone Miner Res., 1994, 1935-1943, 9(12).

Fang, Jia-You et al, In Vitro and in Vivo Evaluations of the Efficacy and Safety of Skin Permeation Enhancers Using Flurbiprofen as a Model Drug, International Journal of Pharmaceutics, 2003, 153-166, 255.

Faulkner, Robert, Aqueous Humor Concentrations of Bimatoprost Free Acid, Bimatoprost and Travoprost Free Acid in Cataract Surgical Patients administered Multiple Topical Ocular Doses of Lumigan or Travatan, Journal of Ocular Pharmacology and Therapeutics, 2010, 147-156, 26(2).

FDA Approves Two New intraocular Pressure Lowering Drugs for the Management of Glaucoma, Mar. 16, 2001, FDA News.

Fiscella, Richard, Peek into the Drug Pipeline, Review of Optometry Online, Jan. 15, 2001, 5 pages.

Fitzpatrick, F.A., Separation of Prostaglandins and Thromboxanes by Gas Chromatography with Glass Capillary Columns, Analytical Chemistry, 1978, 47-52, 50(1).

Flisiak, Robert et al, Effect of Misoprostol on the Course of Viral Hepatitis B, Hepato-Gastroenterology, 1997, 1419-1425, 44.

(56) References Cited

OTHER PUBLICATIONS

Frenkel, R E et al, Evaluation of Circadian Control of Intraocular Pressure After a Single Drop of Bimatoprost 0.03% or Travoprost 0.004%, Curr. Med. Res. Opin., Apr. 2008, 919-923, 24(4).
Funk, Colin et al, Cloning and Expression of a cDNA for the Human Prostaglandin E Receptor EP1 Subtype*, The Journal of Biological Chemistry, Dec. 15, 1993, 26767-26772, 268(35).
Gandolfi, Stefano, Three-month Comparison of Bimatoprost and Latanoprost in Patients With Glaucoma and Ocular Hypertension, Adv. Ther., 2001, 110-121, 18.
Garadi, R et al, Travoprost: A New Once-Daily Dosed Prostaglandin For The Reduction of Elevated Intraocular Pressure, Investigative Ophthalmology & Visual Science, 1999, 4378-B181, Abstract Only.
Geng, Ling et al, Misoprostol, A PGE1 Analog That is Radioprotective for Murine Intestine and Hair, Induces Widely Different Cytokinetic Changes in These Tissues, The Journal of Investigative Dermatology, 1996, 858, 106(4).
Geng, Ling et al, Topical or Systemic 16,16 dm Prostaglandin E2 or WR-2721 (WR-1065) Protects Mice From Alopecia After Fractionated Irradiation, Int. J. Radiat. Biol., 1992, 533-537, 61(4).
Gerth, Jeff et al, Drug Makers Reap Profits on Tax-Backed Research, Apr. 23, 2000, 10 pages, New York Times.
Giuffre, Giuseppe, The Effects of Prostaglandin F2α in the Human Eye, Graefe's Archive Clin. & Exper. Ophthal., 1985, 139-141, 222.
Green Tea Consumption Grows Hair, Protects Against UV Radiation in Animal Models, 2010, 4 Pages, www.hairloss-research.org/blog/?p=4.
Grice, Jeffrey et al, Relative Uptake of Minoxidil into Appendages and Stratum Corneum and Permeation Through Human Skin in Vitro, Journal of Pharmaceutical Sciences, Feb. 2010, 712-718, 99(2).
Griffin, Brenda et al, AL-8810: A Novel Prostaglandin F2α Analog with Selective Antagonist Effects at the Prostaglandin F2α (FP) Receptor, Journal of Pharmacology and Experimental Therapeutics, 1999, 1278-1284, 290(3).
Grow (Verb) Definition, Merriam Webster's Dictionary, Retrieved from http://www.merriam-webster.com/dictionary/growing on Jul. 9, 2012.
Hall, Alistair et al, Clinprost Tijin, Current Opinion in Cardiovascular, Pulmonary & Renal Investigational Drugs, 1999, 605-610, 1(5).
Hallinan, Ann et al, Aminoacetyl Moiety as a Potential Surrogate for Diacylhydrazine Group of SC-51089, a Potent PGE2 Antagonist, and Its Analogs, J Med Chem, 1996, 609-613, 39.
Hanson, W R et al, 16,16 dm Prostaglandin2 Protects From Acute Radiation-Induced Alopecia in Mice, Clinical Research, 1988, 906A, 36(6).
Hanson, W R et al, Subcutaneous or Topical Administration of 16,16 Dimethyl Prostaglandin E2 Protects From Radiation-Induced Alopecia in Mice, Int. J. Radiation Oncology Biol. Phys., 1992, 333-337, 23.
Hartke, J.R. et al, Prostanoid FP Agonists Build Bone in the Ovariectomized Rat, Prostanoid FP Agonists Build Bone in the Ovariectomized Rat, 1999, S207.
Hayashi, Masaki et al, Prostaglandin Analogues Possessing Antinidatory Effects. 1. Modification of the ψ Chain, J. Med. Chem., 1980, 519-524, 23.
Hecker, Markus et al, Studies on the Interaction of Minoxidil with Prostacyclin Synthase in Vitro, Biochemical Pharmacology, 1988, 3363-3365, 37(17).
Hellberg, Mark et al, The Hydrolysis of the Prostaglandin Analog Prodrug Bimatoprost to 17-Phenyltrinor PGF2α by Human and Rabbit Ocular Tissue, J. Ocular Pharmacol. Ther., 2003, 97-103, 19(2).
Higginbotham et al., One-Year, Randomized Study Comparing Bimatoprost and Timolol in Glaucoma and Ocular Hypertension, Archives of Opthalmology, Oct. 2002, 1286-1293, 120 (10).
Houssay, Alerto, Effects of Prostaglandins Upon Hair Growth in Mice, Acta Physiol. Latinoam., 1976, 186-191, 26.
Huang, A. et al, Different Modes of Inhibition of Increase in Cytosolic Calcium and Aggregation of Rabbit Platelets by Two Thromboxane A2 Antagonists, Asia Pacific Journal of Pharmacology, 1994, 163-171, 9.

Hulan H.W. et al, The Development of Dermal Lesions and Alopecia in Male Rats Fed Rapeseed Oil, Canadian Journal of Physiology and Pharmacology, 1976, 1-6, 54(1).
Hulan, H.W. et al, The Effect of Long-Chain Monoenes on Prostaglandin E2 Synthesis by Rat Skin, Lipids, 1977, 604-609, 12(7).
Ichikawa, A. et al, Molecular Aspects of the Structures and Functions of the Prostaglandin E Receptors, J. Lipid Mediators Cell Signalling, 1996, 83-87, 14.
Informa UK Ltd., AGN-192024, 2006.
Inoue, Hironishi, Thromboxane A2 receptor antagonists, Oct. 1996, 1221-1225, 32(10), Pharmaceutical Society of Japan.
J AM Pharm Assoc-, Agents for Glaucoma, New Drugs of 2001, 2001, 4 pages, 42(2), Journal of the American Pharmaceutical Association, http://www.edscape.com/viewarticle/436631_22.
Jakobsson, Per-Johan et al, Membrane-Associated Proteins in Eicosanoid and Glutathione Metabolism (MAPEG), American Journal of Respiratory and Critical Care Medicine, 2000, S20-S24, 161.
Johnstone, M.A., Brief Latanoprost RX Induces Hypertrichosis, Glaucoma Clinical Pharmacology II Poster Presentation, 1998, S258, 39(4).
Johnstone, Murray et al, Prostaglandin-Induced Hair Growth, Survey of Ophthalmology, Aug. 2002, S185-S202, 47(Suppl 1).
Johnstone, Murray, Hypertrichosis and Increased Pigmentation of Eyelashes and Adjacent Hair in the Region of the Ipsilateral Eyelids of Patients Treated With Unilateral Topical Latanoprost, American Journal of Ophthalmology, 1997, 544-547, 124(4).
Jordan, B.A. et al, G-Protein-Coupled Receptor Heterodimerization Modulates Receptor Function, Nature, Jun. 17, 1999, 697-700, 399(6737).
Karim, S.M. et al, Prostaglandins and Human Respiratory Tract Smooth Muscle: Structure Activity Relationship, Advances in Prostaglandin and Thromboxane Research, 1980, 969-980, 7.
Karuss, Achim et al, Evidence for Human Thromboxane Receptor Heterogeneity Using a Novel Series of 9,11-Cyclic Carbonate Derivatives of Prostaglandin F2α, British Journal of Pharmacology, 1996, 1171-1180, 117.
Katz, L.J. et al, Comparison of Human Ocular Distribution of Bimatoprost and Latanoprost, 2010, P450.
Kaufman, Paul, Effects of Intracamerally Infused Prostaglandins on Outflow Facility in Cynomolgus Monkey Eyes with Intact or Retrodisplaced Ciliary Muscle, Experimental Eye Research, 1986, 819-827, 43.
Kende, Andrew et al, Prostaglandin Phosphonic Acids Through Homolytic Halodecarboxylation of Prostaglandins F1α and F2α, Tetrahedron Letters, 1999, 8189-8192, 40.
Kerstetter, J.R. et al, Prostaglandin F2α-1-Isopropylester Lowers Intraocular Pressure Without Decreasing Aqueous Humor Flow, American Journal of Ophthalmology, 1988, 30-34, 105.
Kiriyama, Michitaka et al, Ligand Binding Specificities of the Eight Types and Subtypes of the Mouse Prostanoid Receptors Expressed in Chinese Hamster Ovary Cells, British Journal of Pharmacology, 1997, 217-224, 122.
Kluender, Harold et al, The Synthesis of Dimethylphosphonoprostaglandin Analogs, Prostaglandins and Medicine, 1979, 441-444, 2.
Kreilgaard, Mads, Influence of Microemulsions on Cutaneous Drug Delivery, Advanced Drug Dellivery Reviews, 2002, S77-S98, 54 Suppl. 1.
Kvedar, Joseph et al, Topical Minoxidil in the Treatment of Male Pattern Alopecia, Pharmacotherapy, 1987, 191-197, 7(6).
Lachgar, S. et al, Effect of VEGF and Minoxidil on the Production of Arachidonic Acid Metabolites by Cultured Hair, Dermal Papilla Cells, Eur. J. Dermatol, 1996, 365-368, 6.
Lachgar, S. et al, Hair Dermal Papilla Cell Metabolism is Influenced by Minoxidil, Fundamental & Clinical Pharmacology, 1997, 178, 11(2).
Lachgar, S. et al, Modulation by Minoxidil and VEGF of the Production of Inflammatory Mediators by Hair Follicle Dermal Papilla Cells, Groupe de Rocherche Dermatologique, 1995, 161, 104(1).
Lambert, Joseph, Clinical Study Report, a Multicenter, Double-Masked, Randomized, Parallel, 3-Month study (with Treatment Extended to 1 year) of the Safety and Efficacy of AGN 192024 0.03%

(56) References Cited

OTHER PUBLICATIONS

Ophthalmic Solution Administered Once-Daily or Twice-daily Compared with Timolol 0.5% Ophthalmic Solution Administered Twice-Daily in Subjects with Glaucoma or Ocular Hypertension, Study No. 192024-009, Phase 3, 1998, 34 pages, Allergan, Inc.

Lardy, C. et al, Antiaggregant and Antivasospastic Properties of the New Thromboxane A2 Receptor Antagonist Sodium 4-[[1-[[[(4 Chlorophenyl)sulfony]amino]methyl]cyclopentyl]methyl]benzene-acetate, Arzneim.-Forsch./Drug Res., 1994, 1196-1202, 44(11).

Lee, Ping-Yu et al, The Effect of Prostaglandin F2α on Intraocular Pressure in Mormotensive Human Subjects, Investigative Ophthalmology & Visual Science, Oct. 1988, 1474-1477, 29(10).

Lee, Vincent et al, Improved Ocular Drug Delivery with Prodrugs, Prodrugs: Topical and Ocular Drug Delivery, 1992, 221-297, Kenneth Sloan Edition.

Liang, Y. et al, Identification and Pharmacological Characterization of the Prostaglandin FP Receptor and FP Receptor Variant Complexes, Br. J. Pharmacol., 2008, 1079-1093, 154.

Liljebris, Charlotta et al, Derivatives of 17-Phenyl-18,19,20-trinorprostaglandin F2α Isopropyl Ester: Potential Antiglaucoma Agents, J. Med. Chem., 1995, 289-304, 38.

Ling, Geng et al, 16,16 dm Prostaglandin E2 Protects Mice From Fractionated Radiation-Induced Alopecia, Clinical Research, 1990, 858A, 38(3).

Lumigan Package Insert, Mar. 2001, 6 pages, NDA 21-275.

Lundy, M.W. et al, Restoration of Cancellous Architecture and Increased Bone Strength in Aged Osteopenic Rats Treated with Fluprostenol, 21st Annual Meeting of the American Society for Bone and Mineral Research, 1999, S401.

Maddox, Yvonne et al, Amide and I-amino Derivatives of F Prostaglandins as Prostaglandin Antagonists, Nature, Jun. 15, 1978, 549-552, 273.

Malkinson, Frederick et al, Prostaglandins Protect Against Murine Hair Injury Produced by Ionizing Radiation of Doxorubicin, J. Invest Dermatol., 1993, 135S-137S, 101.

Mansberger, Steven et al, Eyelash Formation Secondary to Latanoprost Treatment in a Patient With Alopecia, Arch. Opthalmol., 2000, 718-719, 118.

Maruyama, Takayuki et al, EP1 Receptor Antagonists Suppress Tactile Allodynia in Rats, Prostaglandins & Other Lipid Mediators, 1999, 217(Abstract), 59.

Matsumura, H. et al, Brain and Neuroscience, 1998, 79-89.

Maurer, Marcus et al, Hair Growth Modulation by Topical Immunophilin Ligands, American Journal of Pathology Apr. 1997, 1433-1441, 150(4).

Maw, Graham, Chapter 8. Pharmacological Therapy for the Treatment of Erectile Dysfunction, Annual Reports in Medicinal Chemistry, 1999, 71-80.

Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).

McCullough, Peter et al, Ridogrel Janssen, Current Opinion in Antiinflammatory & Immunodulatory Investigational Drugs, 1999, 265-276, 1(3).

McMurry, John, Amides, Organic Chemistry, 1984, 794.

Medical Review, Application No. 21-275, Center for Drug Evaluation and Research, 2001.

Medline, Bimatoprost (Ophthalmic), Bimatoprost, Jul. 24, 2001, 4 pages, Medlineplus. Health Information, Online.

Michelet, Jean-Francois et al, Activation of Cytoprotective Prostaglandin Synthase-1 by Minoxidil as a Possible Explanation for Its Hair Growth-Stimulating Effect, J. Invest. Dermatol., 1997, 205-209, 108.

Mihele, Densia et al, Cercetarea Actiunii Hepatoprotectoare a Unor Prostaglandine De Sinteza, Farmacia, 1999, 43-58, 67(5).

Millikan, Larry, Treatment of Alopecia, The Journal of Clinical Pharmacology, 1987, 715, 27(8).

Millikan, Larry, Treatment of Male Pattern Baldness, Drug Therapy, 1989, 62-73.

Mishima, Hiromu, A Comparison of Latanoprost and Timolol in Primary Open-Angle Glaucoma and Ocular Hypertension, Arch. Opthalmol., 1996, 929-932, 114.

Miyamoto, Terumasa et al, A Comparison in the Efficacy and Safety Between Ramatroban (BAY u 3405) and Ozagrel-HCI for Bronchial Asthma —A Phase III, Multi-Center, Randomized, Double-Blind, Group Comparative Study, 1997, 599-639,.

Mori, S. et al, Effects of Prostaglandin E2 on Production of New Cancellous Bone in the Axial Skeleton of Ovariectomized Rats, Bone, 1990, 103-113, 11.

Muller-Rover, Sven et al, A Comprehensive Guide for the Accurate Classification of Murine Hair Follicles in Distinct Hair Cycle Stages, J. Invest. Dermatol, 2001, 3-15, 117.

Mura, Simona et al, Penetration Enhancer-Containing Vesicles (PEVs) as Carriers for Cutaneous Delivery of Minoxidil, International Journal of Pharmaceutics, 2009, 72-79, 380.

Murakami, T. et al, Effect of Isocarbacyclin Methyl Ester Incorporated in Lipid Microspheres on Experimental Models of Peripheral Obstructive Disease, Drug Res., 1995, 991-994, 45(9).

Narumiya, Shuh et al, Roles of Prostanoids in Health and Disease; Lessons From Receptor-Knockout Mice, Common Disease: Genetic and Pathogenetic Aspects of Multifactorial Diseases, 1999, 261-269.

Neau, Steven, Pharmaceutical Salts, Water-Insoluble Drug Formulation, 2008, 417-435.

Negishi, Manabu et al, Molecular Mechanisms of Diverse Actions of Prostanoid Receptors, Biochimica et Biophysica Acta, 1995, 109-120, 1259.

New Drugs for Glaucoma, FDA Consumer Magazine, May-Jun. 2001.

Norrdin, R.W. et al, The Role of Prostaglandins in Bone in Vivo, Prostaglandins Leukotrienes and Essential Fatty Acids, 1990, 139-149, 41.

Olsen, Elise et al, Transdermal Viprostol in the Treatment of Male Pattern Baldness, J. Am. Acad. Dermatol., 1990, 470-472, 23.

Orlicky, D.J., Negative Regulatory Activity of a Prostaglandin F2α Receptor Associated Protein (FPRP), Prostaglandins, Leukotrienes and Essential Fatty Acids, 1996, 247-259, 54(4).

Ortonne, Jean-Paul et al, Hair Melanins's Hair Color: Ultrastructural and Biochemical Aspects, Journal of the Society for Investigative Dermatology, 1993, 82S-89S.

Paragraph IV Letter, Jul. 26, 2010.

Paus, Ralf et al, The Induction of Anagen Hair Growth in Telogen Mouse Skin by Cyclosporine a Administration, Laboratory Investigation, 1989, 365-369, 60(3).

Pfeiffer, N, New Developments in Glaucoma Drug Therapy, Ophthalmologist, 1992, W1-W13, 89.

Pharmaprojects No. 6321, 2006, 1 page.

Phase 3 Lumigan —AGN 192024—Data Presented At American Academy of Ophthalmology, Allergan Press Release, Mar. 1, 2000.

Physicians' Desk Reference, 56th ed., pp. 212-13, 543, 553-54, 2864-65 (2002).

Poyer, J.F. et al, Prostaglandin F2α Effects on Isolated Rhesus Monkey Ciliary Muscle, Invest. Ophthalmol. Vis. Sci., Nov. 1995, 2461-2465, 36(12).

Preparation of '404 Patent Documents for European Patent Office; Defendant Athena Cosmetics, Inc., Supplemental Invalidity Contentions Pursuant to Patent Local Rule 3-3, 2009.

Preparation of '404 Patent Documents for European Patent Office; Defendant Peter Thomas Roth Labs LLC and Peter Thomas Roth, Inc.'s Invalidity Contentions Pursuant to Patent Local Rule 3-3, 2009.

Preparation of '404 Patent Documents for European Patent Office; Defendants Metrics LLC, Product Innovations LLC; Stella International LLC; and Nutra-Luxe, M.D. LLC's; Local Patent Rule 3-3 Preliminary Invalidity Contentions, 2009.

Preparation of '404 Patent Documents for European Patent Office; Invalidity Contentions Pursuant to Patent Local Rule 3-3, 2008.

Rampton, D.S. et al, Anti-inflammatory Profile in Vitro of Ridogrel, A Putative New Treatment for Inflammatory Bowel Disease, Immunology, Microbiology, and Inflammatory Disorders, 1999, G3477.

Resul, B et al, Phenyl-substituted Prostaglandins: Potent and Selective Antiglaucoma Agents, J. Med. Chem., Jan. 22, 1993, 243-248, 36(2).

(56) References Cited

OTHER PUBLICATIONS

Reynolds, A, Darkening of Eyelashes in a Patient Treated With Latanoprost, Eye, 1998, 741-743, 12.

Rigaudy, J. et al, Nomenclature of Organic Chemistry Sections A, B. C, D, E, F, and H, InCL Union of Pure & Applied Chemistry, Organic Chemistry Div., Comm 'n. On Nomenclature of Organic Chemistry, 1979, 255-256.

Roenigk, Henry, New Topical Agents for Hair Growth, Clinics in Dermatology, 1988, 119-121, 6(4).

Romano, Maria Rosaria et al, Evidence for the Involvement of Cannabinoid DB1 Receptors in the Bimatoprost-Induced Contractions on the Human Isolated Ciliary Muscle, Investigative Ophthalmology & Visual Science, Aug. 2007, 3677-3382, 48(8).

Roseborough, Ingrid et al, Lack of Efficacy of Topical Latanoprost and Bimatoprost Ophthalmic Solutions in Promoting Eyelash Growth in Patients with Alopecia Areata, J Am Acad Dermtol, Apr. 2009, 705-706, 60(4).

Ruel, Rejean et al, New Class of Biphenylene Dibenzazocinones as Potent Ligands for the Human EP1 Prostanoid Receptor, Bioorganic & Medicinal Chemistry Letters, 1999, 2699-2704, 9.

Saeki, Hideshisa et al, Guidelines for Management of Atopic Dermatitis, Journal of Dermatology, 2009, 563-577, 36.

Sakuma, Yoko et al, Crucial Involvement of the EP4 Subtype of Prostaglandin E Receptor in Osteoclast Formation by Proinflammatory Cytokines and Lipopolysacharide, Journal of Bone and Mineral Research, 2000, 218-227, 15(2).

Sauk, John et al, Influence of Prostaglandins E1, E2, and Arachidonate on Melanosomes in Melanocytes and Keratinocytes of Anagen Hair Bulbs in Vitro, The Journal of Investigative Dermatology, 1975, 332-337, 64.

Scheider, Marlon et al, The Hair Follicle as a Dynamic Miniorgan, Current Biology, 2009, R132-R142, 19.

Sharif, N.A. et al, [3H]AL-5848 ([3H]9β-(+)-Fluprostenol). Carboxylic Acid of Travoprost (AL-6221), a Novel FP Prostaglandino Study the Pharmacology and Autoradiographic Localization of the FP Receptor, J. Pharm. Pharmacol., 1999, 685-694, 51.

Sharif, N.A. et al, Cat Iris Sphincter Smooth-Muscle Contraction: Comparison of FP-Class Prostaglandin Analog Agonist Activities, J. Ocul. Pharmacol. Ther, Apr. 2008, 152-163, 24(2).

Sharif, N.A. et al, Human Ciliary Muscle Cell Responses to FP-class Prostaglandin Analogs: Phosphoinositide Hydrolysis, Intracellular Ca2+ Mobilization and MAP Kinase Activation, J. Ocul. Pharmacol Ther., 2003, 437-455, 19.

Sharif, N.A. et al, Human Trabecular Meshwork cell Responses Induced by Bimatoprost, Travoprost, Unoprostone, and Other FP Prostaglandin Receptor Agonist Analogues, Invest. Ophthalmol Vis. Sci., 2003, 715-721, 44.

Sharif, N.A. et al, Ocular Hypotensive FP Prostaglandin (PG) Analogs: PG Receptor Subtype Binding Affinities and Selectivities, and Agonist Potencies at FP and Other PG Receptors in Cultured Cells, Journal of Ocular Pharmacology and Therapeutics, 2003, 501-515, 19(6).

Sharif, N.A. et al, Update and Commentary on the Pro-Drug Bimatoprost and a Putative Prostamide Receptor, Expert Rev. Ophthalmol., 2009, 477-489, 4(5).

Sharif, Najam, Bimatoprost and Its Free Acid Are Prostaglandin FP Receptor Agonists, European Journal of Pharmacology, 2001, 211-213, 432.

Sherwood, Mark et al, Six-Month Comparison of Bimatoprost Once-Daily and Twice-Daily with Timolol Twice-Daily in Patients with Elevated Intraocular Pressure, Survey of Ophthalmology, 2001, S361-S368, 45(4).

Shih, Mei-Shu et al, PGE2 Induces Regional Remodeling Changes in Haversian Envelope: a Histomorphometric Study of Fractured Ribs in Beagles, Bone and Mineral, 1986, 227-264, 1.

Shimazaki, Atsushi et al, Effects of the New Ethacrynic Acid Derivative SA9000 on Intraocular Pressure in Cats and Monkeys, Biol. Pharm. Bull., 2004, 1019-1024, 27(7).

Shimazaki, Atsushi et al, New Ethacrynic Acid Derivatives as Potent Cytoskeletal Modulators in Trabecular Meshwork Cells, Bio. Pharm. Bull., 2004, 846-850, 27(6).

Sjoquist, Birgitta et al, Ocular and Systemic Pharmacokinetics of Latanoprost in Humans, Surv. Ophthalmol., Aug. 2002, S6-S12, 47(Suppl 1).

Sjoquist, Birgitta et al, Pharmacokinetics of Latanoprost in the Cynomolgus Monkey. 3rd Communication: Tissue Distribution After Topical Administration on the Eye Studied by Whole Body Autoradiography, Glaucoma Research Laboratories. Arzneim-Forsch/Drug Res., 1999, 240-249, 49.

Sorbera, L.A. et al, Travoprost, Drugs of the Future, 2000, 41-45, 25(1).

Souillac, Pierre et al, Characterization of Delivery Systems, Differential Scanning Calorimetry, 1999, 212-227, 49.

Spada, C.S. et al, Bimatoprost and Prostaglandin F2α Selectively Stimulate Intracellular Calcium Signaling in Different Cat iris Sphincter Cells, Exp. Eye Res., Jan. 2005, 135-145, 80(1).

Sredni, Benjamin et al, The Protective Role of the Immunomodulator AS101 Against Chemotherapy-Induced Alopecia Studies on Human and Animal Models, Int. J. Cancer, 1996, 97-103, 65.

Stahl, Heinrich et al, Chapter 12: Monographs on Acids and Bases, Handbook of Pharmaceutical Salts, 2008, 265-327.

Stamer, W.D. et al, Cellular Basis for Bimatoprost Effects on Human Conventional Outflow, Invest. Ophthalmol. Vis. Sci., Oct. 2010, 5176-5181, 51(10).

Stjernschantz, Johan et al, From PGF2α -isopropyl Ester to Latanoprost: A Review of the Development of Xalatan: The Proctor Lecture, Invest. Ophthalmol. Vis. Sci., May 2001, 1134-1145, 42(6).

Stjernschantz, Johan et al, Phenyl Substituted Prostaglandin Analogs for Glaucoma Treatment, Phenyl Substituted Prostaglandin Analogs for Glaucoma Treatment, 1992, 691-704, 17(8).

Stjernschantz, Johan et al, Studies on Ocular Inflammation and Development of a Prostaglandin Analogue for Glaucoma Treatment, Exp. Eye Res., Apr. 2004, 759-766, 78(4).

Supplement A (Lumigan®), Physician's Desk Reference 2001, Mar. 2001.

Swarbrick, James et al, Salt Forms of Drugs and Absorption, Encyclopedia of Pharmaceutical Technology, 1988, 453-499, 13.

Terada, Nobuhisa et al, Effect of a Thromboxane A2 Receptor Antagonist Ramatroban (BAY u 3405), on Inflammatory Cells, Chemical Mediators and Non-Specific Nasal Hyperreactivity After Allergen Challenge in Patients with Perennial Allergic Rhinitis, Allergoloy International, 1998, 59-67, 47.

The Newsletter of Glaucoma Foundation, 2000, 11 pages, 11(2).

Titus, Reuben, Alloe Vera—The Magical Plant Amongst Us, 2009, 12 pages, http://www.scribd.com/doc/19139862/ Aloe-VeraMiracle-Plant.

Tobin, Desmond, Aging of the Hair Follicle Pigmentation System, Int. J. Trichology, Jul.-Dec. 2009, 83-93, 1(2).

Tomita, Yasushi et al, Melanocyte-Stimulating Properties of Arachidonic Acid Metabolites: Possible Role in Postinflammatory Pigmentation, Pigment Cell Research, 1992, 357-361, 5.

Topical Emu Oil and Coconut Oil for Hair Loss—A Potent Combination, 2010, 3 pages, www.hairloss-research.org/ blog/?p=15.

Travatan (travoprost ophthalmic solution) 0.004% Product Insert, NDA 21-257, Mar. 16, 2001, 7 Pages.

U.S. Appl. No. 11/805,122, Resp. to Office Action dated Jan. 21, 2009.

Ueda, Ken et al, Cortical Hyperostosis Following Long-Term Administration of Prostaglandin E1 in Infants with Cyanotic Congenital Heart Disease, Journal of Pediatrics, 1980, 834-836, 97(5).

Uno, Hideo et al, Effect of Latanoprost on Hair Growth in the Bald Scalp of the Stump-Tailed Macacque: A Pilot Study, Acta Derm Venereol, 2002, 7-12, 82.

Van Alphen, G.W.H.M. et al, The effect of Prostaglandins on the Isolated Internal Muscles of the Mammalian Eye, Including Man, Documenta Ophthalmologica, 1977, 397-415, 42(4).

Vandenburg, A.M. et al, A One-Month Dose Response Study of AGN 192024, A Novel Antiglaucoma Agent, in Patients with Elevated Intraocular Pressure, Glaucoma Clinical Pharmacology IV Poster Presentation, 1999, S830, 40 (4).

(56) References Cited

OTHER PUBLICATIONS

Vandenburgh, Amanda, reply to Alan L. Robin, An Accurate Comparison of Bimatoprost's Efficacy and Adverse Effects, Arch Ophthalmol, Jul. 2002, 997-1000, 120.

Vayssairat, Michael, Preventive Effect of an Oral prostacyclin Analog, Beraprost Sodium, on Digital Necrosis in Systemic Sclerosis, J. Rheumatol, 1999, 2173-2178, 26.

Vengerovsky, A.I. et al, Hepatoprotective action of prostaglandins, Experimental and Clinical Pharmacology, 1997, 78-82, 60(5).

Verbeuren, T. et al, The TP-Receptor Antagonist S 18886 Unmasks Vascular Relaxation and Potentiates the Anti-Platelet Action of PGD2, New Antithrombotic Agents, Jun. 11, 1997, 693.

Verma, DD et al, Treatment of Alopecia Areata in the DEBR Model Using Cyclosporin a Lipid Vesicles, Eur. J. Dermatol, 2004, 332-338, 14.

Vielhauer, G.A. et al, Cloning and Localization of hFP(S): a Six-Transmembrane mRNA Splice Variant of the Human FP Prostanoid Receptor, Arch Biochem Biophys., Jan. 15, 2004, 175-185, 421(2).

Villumsen, J. et al, Prostaglandin F2α-isopropylester Eye Drops: Effect on Intraocular Pressure in Open-Angle Glaucoma, Br. J. Ophthalmol., 1989, 975-979, 73.

Vincent, J.E. et al, Letter to the Editor Prostaglandin Synthesis and Selenium Deficiency a Hypothesis, Prostaglandins, 1974, 339-340, 8(4).

Vippagunta, Sudha et al, Crystalline Solids, Advanced Drug Delivery Reviews, 2001, 3-26, 48.

Waddell, K.A. et al, Combined Capillary Column Gas Chromatography Negative Ion Chemical Ionization Mass Spectrometry of Prostanoids, Biomedical Mass Spectrometry, 1983, 83-88, 10(2).

Wand, Martin, Latanoprost and Hyperpigmentation of Eyelashes, Arch Ophthalmology, Sep. 1997, 1206-1208, 115.

Wang, Yili et al, Design and Synthesis of 13,14-Dihydro Prostaglandin F1α Analogues as Potent and Selective Ligands for the Human FP Receptor, J. Med. Chem., 2000, 945-952, 43.

Watson, Peter et al, A Six-month, Randomized, Double-masked Study Comparing Latanoprost with Timolol in Open-Angle Glaucoma and Ocular Hypertension, Ophthalmology, 1996, 126-137, 103.

Whitcup, A Multi-Center, Investigator-Marked, Randomized, Parallel Study of the Safety and Efficacy of AGN 192024 0.03% Ophthalmic Solution Compared with Latanoprost 0.005% Ophthalmic Solution Administered Once-Daily in Subjects with Glaucoma or Ocular Hypertension, Study No. 192024-010-01, Phase 3b, 1999, 1.

White, J.H. et al, Heterodimerization is Required for the Formation of a Functional GABA(B) Receptor, Nature, Dec. 17, 1998, 679-682, 396(6712).

Whitson, Jess, Travoprost—a New Prostaglandin Analogue for the Treatment of Glaucoma, Expert Opin. Pharmacother, 2002, 965-977, 3 (7).

Willis, Anthony, Prostaglandins and Related Lipids, vol. I, Chemical and Biochemical Aspects, CRC Handbook of Eicosanoids, 1987, 80-97, 1.

Wilson, S.J. et al Dimerization of the Human Receptors for Prostacyclin and Thromboxane Facilitates Thromboxane Receptor-Mediated T CAMP Generation, J. Biol. Chem., Dec. 17, 2004, 53036-53047, 279(51).

Woodward, David et al, Bimatoprost Effects on Aqueous Humor Dynamics in Monkeys, J. Ophthalmol., 2010, 1-5, vol. 2010.

Woodward, David et al, Bimatoprost: a Novel Antiglaucoma Agent, Cardiovascular Drug Reviews, 2004, 103-120, 22(2).

Woodward, David et al, Emerging Evidence for Additional Prostanoid Receptor Subtypes, Current Topics in Pharmacology, 1998, 153-162, 4.

Woodward, David et al, Identification of an antagonist that selectively blocks the activity of prostamides (prostaglandin-ethanolamides) in the feline iris, British Journal of Pharmacology, 2007, 342-352, 150.

Woodward, David et al, Molecular Characterization and Ocular Hypotensive Properties of the Prostanoid EP2 Receptor, Journal of Ocular Pharmacology, 1995, 447-454, 11(3).

Woodward, David et al, Prostaglandin F2α (PGF2α) 1-Ethanolamide: A Unique Local Hormone Biosynthesized From Anandamide, 11th Intl Conf. Advances Prostaglandin & Leukotriene Res.: Basic Sci. & New Clinical Applications—Abstract Book 27, 2000, 1 page.

Woodward, David et al, Replacement of Carboxylic Acid Group of Prostaglandin F2α with a Hydroxyl or Methoxy Substituent Provides Biologically Unique Compounds, British Journal of Pharmacology, Aug. 2000, 1933-1943, 130(8).

Woodward, David et al, Studies on the Ocular Effects of Pharmalogically Novel Agent Prostaglandin F2α 1- OCH3 (AGN 191129), Eicosanoids, 1998, R719.

Woodward, David et al, The Pharmacology of Bimatoprost (LumiganTM), Sury Ophthalmol, 2001, S337-S345, Suppl 4.

Woodward, David, Pharmacological Characterization of a Novel Antiglaucoma Agent, Bimatoprost (AGN 192024), J. Pharmacol. Exp. Ther., Jan. 24, 2003, 772-785, 305 (2).

Xalatan (Latanoprost Ophthalmic Solution) 0.005% Product Insert, 2001, 4 Pages.

Xalatan ® Eye Drops, Retrieval Date : Oct. 2, 2010, 3 pages, http://home.intekom.com/pharm/pharmaca/xalatan.html.

Yamaji, K. et al, Prostaglandins E1 and E2, but not F2α or Latanoprost, Inhibit Monkey Ciliary Muscle Contraction, Curr. Eye Res., Aug. 2005, 661-665, 30(8).

Zeigler, Tania, Old Drug New Use: New Research Shows Common Cholesterol-Lowering Drug Reduces Multiple Sclerosis in Mice, National Institute of Neurological Disorders and Stroke, Jan. 6, 2003, 2 Pages.

Zimbric, M.L. et al, Effects of Latanoprost of Hair Growth in the Bald Scalp of Stumptailed Macaques, Glaucoma Pharmacology, Cellular Mechanism II, 1999, 3569-B427—Abstract, vol. 40, No. 4.

FDA Label for Approved NDA 22-184 of Lumigan 0.01% and Lumigan 0.03%, Aug. 31, 2010.

Cantor, Louis et al, Reply-Bimatoprost, the Prodrug of a Prostaglandin Analogue, Br J Ophthalmol, 2008, 863-864, 92.

Darnell, J., Cell-to-Cell Signaling: Hormones and Receptors, Molecular Cell Biology, 1990, 738-743, vol. 82, Darnell, J., Lidish, H., Baltimore, D., Eds., New York, New York.

* cited by examiner

COMPOUNDS AND METHODS FOR ENHANCING HAIR GROWTH

CROSS-REFERENCE TO RELATED APPLICATION

This application claims the benefit of U.S. Provisional Application Ser. No. 61/435,126, filed Jan. 21, 2011, the disclosure of which is hereby incorporated in its entirety herein by reference.

FIELD OF THE INVENTION

This invention relates to a method for stimulating the growth of mammalian hair comprising the application to mammalian skin of a 3, 7 or 3 and 7 thia or oxa prostanoic acid derivative or a pharmacologically acceptable salt thereof, alone, or in association with a topical pharmaceutical carrier.

BACKGROUND OF THE INVENTION

Dermatologists recognize many different types of hair loss, the most common by far being "alopecia" wherein human males begin losing scalp hair at the temples and on the crown of the head as they get older. While this type of hair loss is largely confined to males, hence its common name "male pattern baldness," it is not unknown in women. No known cure has yet been found despite continuing attempts to discover one.

A good deal is known about various types of human hair and its growth patterns on various parts of the body.

For purposes of the present invention, it is necessary to consider various types of hair, including, terminal hairs and vellus hairs and modified terminal hairs, such as seen in eye lashes and eye brows. Terminal hairs are coarse, pigmented, long hairs in which the bulb of the hair follicle is seated deep in the dermis. Vellus hairs, on the other hand, are fine, thin, non-pigmented short hairs in which the hair bulb is located superficially in the dermis. As alopecia progresses, a transition takes place in the area of approaching baldness wherein the hairs themselves are changing from the terminal to the vellus type.

Another factor that contributes to the end result is a change in the cycle of hair growth. All hair, both human and animal, passes through a life cycle that includes three phases, namely, the anagen phase, the catagen phase and the telogen phase. The anagen phase is the period of active hair growth and, insofar as scalp hair is concerned, this generally lasts from 3-5 years. The catagen phase is a short transitional phase between the anagen and telogen phases which, in the case of scalp hair, lasts only 1-2 weeks. The final phase is the telogen phase which, for all practical purposes, can be denominated a "resting phase" where all growth ceases and the hair eventually is shed preparatory to the follicle commencing to grow a new one. Scalp hair in the telogen phase is also relatively short-lived, some 3-4 months elapsing before the hair is shed and a new one begins to grow.

Under normal hair growth conditions on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

Alopecia is associated with the severe diminution of hair follicles. A bald human subject will average only about 306 follicles per square centimeter, whereas, a non-bald human in the same age group will have an average of 460 follicles per square centimeter. This amounts to a one-third reduction in hair follicles which, when added to the increased proportion of vellus hair follicles and the increased number of hair follicles in the telogen phase, is both significant and noticeable. Approximately 50% of the hairs must be shed to produce visible thinning of scalp hair. It is thus a combination of these factors: transition of hairs from terminal to vellus, increased number of telogen hairs—some of which have been shed, and loss of hair follicles that produces "baldness".

While a good deal is known about the results of male pattern baldness, very little is known about its cause. The cause is generally believed to be genetic and hormonal in origin although, the known prior art attempts to control it through hormone adjustment have been singularly unsuccessful.

One known treatment for male pattern alopecia is hair transplantation. Plugs of skin containing hair are transplanted from areas of the scalp where hair is growing to bald areas with reasonable success; however, the procedure is a costly one in addition to being time-consuming and quite painful. Furthermore, the solution is inadequate from the standpoint that it becomes a practical, if not an economic, impossibility to replace but a tiny fraction of the hair present in a normal healthy head of hair.

Other non-drug related approaches to the problem include such things as ultra-violet radiation, massage, psychiatric treatment and exercise therapy. None of these, however, has been generally accepted as being effective. Even such things as revascularization surgery and acupuncture have shown little, if any, promise.

By far, the most common approach to the problem of discovering a remedy for hair loss and male pattern alopecia has been one of drug therapy. Many types of drugs ranging from vitamins to hormones have been tried and only recently has there been any indication whatsoever of even moderate success. For instance, it was felt for a long time that since an androgenic hormone was necessary for the development of male pattern baldness, that either systemic or topical application of an antiandrogenic hormone would provide the necessary inhibiting action to keep the baldness from occurring. The theory was promising but the results were, for the most part, disappointing.

The androgenic hormone testosterone was known, for example, to stimulate hair growth when applied topically to the deltoid area as well as when injected into the beard and pubic regions. Even oral administration was found to result in an increased hair growth in the beard and pubic areas as well as upon the trunk and extremities. While topical application to the arm causes increased hair growth, it is ineffective on the scalp and some thinning may even result. Heavy doses of testosterone have even been known to cause male pattern alopecia.

Certain therapeutic agents have been known to induce hair growth in extensive areas of the trunk, limbs and even occasionally on the face. Such hair is of intermediate status in that it is coarser than vellus but not as coarse as terminal hair. The hair is generally quite short with a length of 3 cm. being about maximum. Once the patient ceases taking the drug, the hair reverts to whatever is normal for the particular site after six months to a year has elapsed. An example of such a drug is diphenylhydantoin which is an anticonvulsant drug widely used to control epileptic seizures. Hypertrichosis is frequently observed in epileptic children some two or three months after starting the drug and first becomes noticeable on the extensor aspects of the limbs and later on the trunk and face. (The same pattern of hypertrichosis is sometimes caused by injury to the head.) As for the hair, it is often shed when the drug is discontinued but may, in some circumstances, remain.

Streptomycin is another drug that has been found to produce hypertrichosis, in much the same way as diphenylhydantoin, when administered to children suffering from tuberculous meningitis. About the same effects were observed and the onset and reversal of the hypertrichosis in relation to the period of treatment with the antibiotic leave little question but that it was the causative agent.

Two treatments have been demonstrated as showing some promise in reversing male pattern alopecia. These treatments include the use of a microemulsion cream containing both estradiol and oxandrolone as its active ingredients and the use of organic silicon.

In addition to the foregoing, it has been reported in U.S. Pat. Nos. 4,139,619 and 4,968,812 that the compound minoxidil is useful for the treatment of male pattern baldness. That compound, among others, has proven to have considerable therapeutic value in the treatment of severe hypertension. It is a so-called "vasodilator" which, as the name implies, functions to dilate the peripheral vascular system. Dermatologists and others have recognized that prolonged vasodilation of certain areas of the human body other than the scalp sometimes result in increased hair growth even in the absence of any vasodilating therapeutic agent. For instance, increased hair growth around surgical scars is not uncommon. Similarly, arteriovenous fistula have been known to result in increased vascularity accompanied by enhanced hair growth. Externally-induced vasodilation of the skin, such as, for example, by repeated biting of the limbs by the mentally retarded and localized stimulation of the shoulders by water carries has been known to bring on hypertrichosis in the affected areas. Be that as it may, similar techniques such as continued periodic massage of the scalp have been found to be totally ineffective as a means for restoring lost hair growth to the scalp. Scar tissue on the scalp inhibits rather than promotes hair growth.

Bimatoprost, which is sold by Allergan, Inc. of Irvine, Calif., U.S.A. as LATISSE® ophthalmic solution, has been found to be effective to increase the growth of eyelashes.

It is, therefore, a principal object of the present invention to provide a novel and effective treatment for the stimulation of hair growth and the treatment of male pattern baldness.

Another object of the invention is to provide a method of stimulating hair growth in humans and non-human animals that is compatible with various types of therapeutic agents or carriers and, therefore, would appear to be combinable with those which, by themselves, demonstrate some therapeutic activity such as, for example, microemulsion creams or topical compositions containing estradiol and oxandrolone, minoxidil or agents that block the conversion of testosterone to dihydrotesterone (Procipia).

Still another objective is the provision of a treatment for the stimulation of hair growth which, while effective for its intended purpose, is apparently non-toxic and relatively free of unwanted side effects.

An additional object of the invention herein disclosed and claimed is to provide a method for treating hair loss in men or women which can be applied by the patient under medical supervision no more stringent than that demanded for other topically-administered therapeutic agents.

Other objects of the invention are to provide a treatment for male pattern alopecia which is safe, simple, painless, cosmetic in the sense of being invisible, easy to apply and quite inexpensive when compared with hair transplants and the like.

U.S. Pat. Nos. 6,410,591; 6,538,018: 6,767,920 and 6,956,057 disclose various 3, 7 or 3 and 7 thia or oxa protanoic acid derivatives as agents for lowering intraocular pressure (IOP) are hereby incorporated by reference in their entireties. U.S. Pat. No. 6,956,057 also discloses that $EP_4$ agonists other than the 3, 7 or 3 and 7 thia or oxa protanoic acid derivatives disclosed in said patents lower IOP.

SUMMARY OF THE INVENTION

In the discussion of this invention the following terms have the following meanings:

An "$EP_4$ agonist prodrug" is an inactive precursor of an $EP_4$ agonist drug that is converted into its active form in the body by normal metabolic processes. Preferably, the prodrug is an ester of an $EP_4$ agonist, more preferably an alkyl ester, e.g. a lower alkyl ester of PGE.

An "$EP_4$ agonist" is a compound that binds to the $EP_4$ receptor of a cell and triggers a response by that cell that mimics the action of the naturally occurring endogenous substance that is PGE.

An "$EP_3$ agonist" is a compound that binds to the $EP_3$ receptor of a cell and triggers a response by that cell that mimics the action of the naturally occurring endogenous substance that is PGE.

"Pharmaceutically acceptable salts" refer to those salts which retain the biological effectiveness and properties of the free acid and which are obtained by reaction with inorganic bases such as sodium hydroxide, potassium hydroxide or calcium hydroxide and the like or organic bases such as lysine, arginine, ethanolamine and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, n-propyl, isopropyl, n-butyl, isobutyl, tertiary butyl, pentyl, hexyl and the like. The alkyl group may be optionally substituted with one or more substituents are selected from the group consisting of hydroxyl, cyano, alkoxy, $=O$, $=S$, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, $=O$, $=S$, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino "Alkaryl" refers to an alkyl that is covalently joined to an aryl group. Preferably, the alkyl is a lower alkyl.

"Effective amount" is defined as an amount which is effective in growing hair.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

This invention provides pharmaceutical compositions for topical application to enhance hair growth comprising an effective amount of a 3, 7 or 3 and 7 thia or oxa protanoic

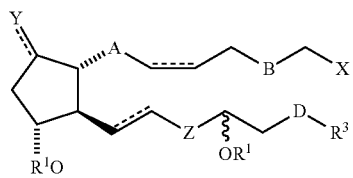

acid derivatives represented by the formula I:

wherein hatched lines represent the a configuration, a triangle represents the 13 configuration and a dotted line represents the presence or absence of a double bond;

A and B are independently selected from the group consisting of O, S and $CH_2$;

provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$ or

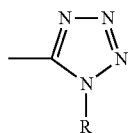

Y is O, halogen or cyano;

Z is $CH_2$ or a covalent bond;

R is H or $R^2$;

$R^1$ is H, $R^2$, phenyl, or $COR^2$;

$R^2$ is $C_1$-$C_5$ lower alkyl or alkenyl and $R^3$ is hydrocarbyl or a substituted derivative thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in association with a pharmaceutical carrier adapted for topical application to mammalian skin.

A preferred group of the compounds of the present invention includes compounds that have the following structural formula II:

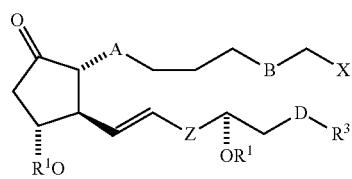

Another preferred group includes compounds having the formula III:

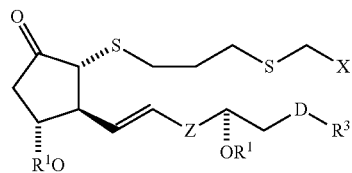

In the above formulae, the substituents and symbols are as hereinabove defined.

In the above formulae:

Preferably, A and B are both S.

Preferably, D represents a covalent bond or is $CH_2$; more preferably D is $CH_2$.

Preferably Z represents a covalent bond.

Preferably R is H.

Preferably $R^1$ is H.

Preferably Y is O.

Preferably X is $CO_2R$ and more preferably R is selected from the group consisting of H, methyl and i-propyl.

Another aspect of the invention provides methods for stimulating the rate of hair growth and for stimulating the conversion of vellus hair or intermediate hair to growth as terminal hair in a human or non-human animal by administering to the skin of the animal an effective amount of a 3, 7 or 3 and 7 thia or oxa prostanoic acid derivatives represented by the formula I:

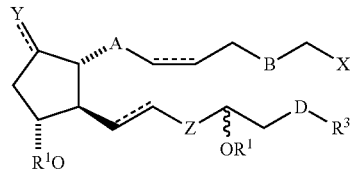

wherein hatched lines represent the a configuration, a triangle represents the β configuration and a dotted line represents the presence or absence of a double bond;

A and B are independently selected from the group consisting of O, S and $CH_2$;

provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$ or

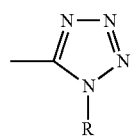

Y is O, halogen or cyano;
Z is CH₂ or a covalent bond;
R is H or $R^2$;
$R^1$ is H, $R^2$, phenyl, or $COR^2$;
$R^2$ is $C_1$-$C_5$ lower alkyl or alkenyl and $R^3$ is hydrocarbyl, or substituted derivatives thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in association with a pharmaceutical carrier adapted for topical application to mammalian skin.

Some other embodiments of the invention are included in the following paragraphs:

1. The method of treating or preventing alopecia caused by chemotherapy which comprises applying to a patient in need thereof an effective amount of a 3, 7 or 3 and 7 thia or oxa prostanoic acid compound represented by the formula I as a foam produced from a foamable liquid composition, wherein said composition comprises one or more of said compounds of formula I, a surfactant, wherein the surfactant optionally includes a foam stabilizer and an aqueous-alcohol solvent, comprising water and an alcohol, which enables said compound to be solubilized.
2. A foamable liquid composition, for use in the method of paragraph 1, comprising one or more of the a 3, 7 or 3 and 7 thia or oxa prostanoic acid compound represented by the formula I and a surfactant, wherein the surfactant optionally includes a foam stabilizer and an aqueous-alcohol solvent, comprising water and an alcohol, which enables said active ingredient to be solubilized.
3. The composition of paragraph 2 wherein said aqueous-alcohol solvent further comprises an acid and a water soluble solvent, wherein said acid is an inorganic acid, or an organic acid containing eight carbons or less and said water soluble solvent is selected from the group consisting of butylene glycol, glycerin, polyglycerin, ethylene glycol, and propylene glycol.
4. The composition of paragraph 3 wherein said alcohol is selected from the group consisting of methanol, ethanol, propanol and mixtures thereof
5. The composition of paragraph 4 wherein said acid is lactic acid and said water soluble solvent is propylene glycol.
6. The composition of paragraph 5 wherein said lactic acid is provided at a concentration of from 0.5 to 5 percent, by weight, of the foamable liquid composition and said propylene glycol is provided in an amount of from 1 to 20 percent, by weight, of the foamable liquid composition
7. The composition of paragraph 6 wherein said alcohol is ethanol and is provided in an amount of from 1 to 50 percent, by weight, of the foamable liquid composition.
8. The composition of paragraph 7 wherein said surfactant is oleth-20 and is provided in an amount of from 0.1 to 5 percent, by weight, of the foamable liquid composition.
9. The composition of paragraph 8 wherein said foam stabilizer is lauryl glucoside and is provided in an amount of from 0.05 to 0.5 percent, by weight, of the foamable liquid composition.

10. A gel comprising a 3, 7 or 3 and 7 thia or oxa prostanoic acid compound represented by the formula I

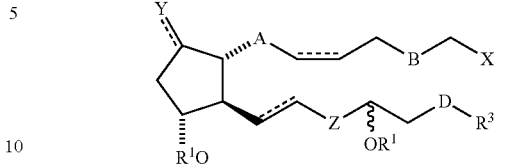

wherein hatched lines represent the α configuration, a triangle represents the β configuration and a dotted line represents the presence or absence of a double bond;
A and B are independently selected from the group consisting of O, S and $CH_2$;
provided that at least one of A or B is S;
D represents a covalent bond or $CH_2$, O, S or NH;
X is $CO_2R$, $CONR_2$, $CH_2OR$, $P(O)(OR)_2$, $CONRSO_2R$, $SONR_2$, tetrazole or triazole;
Y is O, halogen or cyano;
Z is $CH_2$ or a covalent bond;
R is H or $R^2$;
$R^1$ is H, $R^2$, or $COR^2$;
$R^2$ is $C_1$-$C_5$ lower alkyl or alkenyl and $R^3$ is hydrocarbyl or a substituted derivative thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in a pharmaceutically-acceptable solvent, comprising propylene glycol and alcohol and a crosslinked acrylic polymer thickening agent such as a Carbomer, e.g. Carbomer 934P, wherein the crosslinked acrylic polymer thickening agent is neutralized with a neutralizing agent such as diisopropanolamine.

11. A composition in the form of a gel comprising from 0.01% to 10% of a 3, 7 or 3 and 7 thia or oxa prostanoic acid compound represented by the formula I

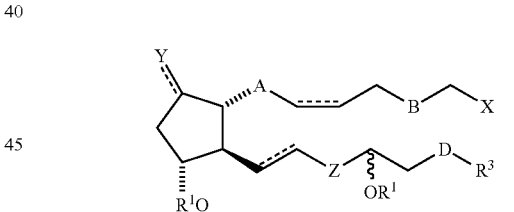

wherein hatched lines represent the α configuration, a triangle represents the β configuration and a dotted line represents the presence or absence of a double bond;
A and B are independently selected from the group consisting of O, S and $CH_2$;
provided that at least one of A or B is S;
D represents a covalent bond or $CH_2$, O, S or NH;
X is $CO_2R$, $CONR_2$, $CH_2OR$, $P(O)(OR)_2$, $CONRSO_2R$, $SONR_2$, tetrazole or triazole;
Y is O, halogen or cyano;
Z is $CH_2$ or a covalent bond;
R is H or $R^2$;
$R^1$ is H, $R^2$, or $COR^2$;
$R^2$ is $C_1$-$C_5$ lower alkyl or alkenyl and $R^3$ is hydrocarbyl or a substituted derivative thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in association with a pharmaceutical carrier adapted for topical application to mammalian skin, by weight, a crosslinked copolymer of acrylic acid as a thickening agent, and a pharmaceutically acceptable solvent.

12. The composition of paragraph 11, wherein said pharmaceutically acceptable solvent is selected from the group consisting of ethanol, propanol, butanol, propylene glycol, dipropylene glycol, hexylene glycol, 1,3-butylene glycol, PEG-200, PEG-400, glycerol and mixtures thereof 13. The composition of paragraph 12, comprising a solvent selected from the group consisting of ethanol, propanol and butanol.

14. The composition of paragraph 13, comprising a solvent selected from the group consisting of ethanol and isopropanol.

15. The composition of paragraph 14, comprising a solvent selected from the group consisting of propylene glycol, dipropylene glycol, hexylene glycol, 1,3-butylene glycol, PEG-200, PEG-400, and glycerol.

16. A composition of paragraph 15, wherein said solvent comprises a mixture comprising a first solvent selected from the group consisting of ethanol, propanol and butanol and a second solvent selected from the group consisting of propylene glycol, dipropylene glycol, hexylene glycol, 1,3-butylene glycol, PEG-200, PEG-400, and glycerol.

17. The composition of paragraph 16, wherein said solvent comprises a mixture of ethanol and propylene glycol.

18. The composition of paragraph 17, further comprising a neutralizing agent.

19. The composition of paragraph 18, wherein said neutralizing agent is selected from the group consisting of ammonium hydroxide, arginine, 2-amino-2-methyl-1-propanol, dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, aminomethyl propanol, sodium hydroxide, and potassium hydroxide.

20. The composition of paragraph 19, wherein said neutralizing agent is selected from the group consisting of 2-amino-2-methyl-1-propanol, diisopropanolamine, triisopropanolamine, and tetrahydroxypropyl ethylenediamine.

21. The composition of paragraph 20, wherein said neutralizing agent is 2-amino-2-methyl-1-propanol.

22. The composition of paragraph 11, wherein said solvent is present in said composition in an amount of at least about 20%.

23. The composition of paragraph 22 which comprises from about 20% to about 99%, by weight, of said solvent.

24. The composition of paragraph 11, wherein said crosslinked copolymer of acrylic acid comprises an acrylate/$C_{10-30}$ alkyl acrylate crosspolymer.

25. The composition of paragraph 24 wherein said solvent is present in said composition in an amount of at least about 20%.

26. A composition in the form of a gel comprising: from about 0.1 to 10% a 3, 7 or 3 and 7

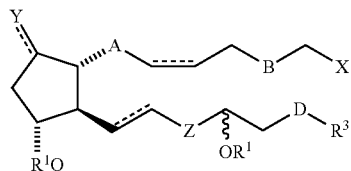

thia or oxa prostanoic acid compound represented by the formula I:
wherein hatched lines represent the α configuration, a triangle represents the β configuration and a dotted line represents the presence or absence of a double bond;
A and B are independently selected from the group consisting of O, S and $CH_2$;
provided that at least one of A or B is S;
D represents a covalent bond or $CH_2$, O, S or NH;
X is $CO_2R$, $CONR_2$, $CH_2OR$, $P(O)(OR)_2$, $CONRSO_2R$, $SONR_2$, tetrazole or triazole;
Y is O, halogen or cyano;
Z is $CH_2$ or a covalent bond;
R is H or $R^2$;
$R^1$ is H, $R^2$, or $COR^2$;
$R^2$ is $C_1$-$C_5$ lower alkyl or alkenyl and $R^3$ is hydrocarbyl or a substituted derivative thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, from about 30% to about 80% of a first solvent selected from the group consisting of propylene glycol, dipropylene glycol, hexylene glycol, 1,3-butylene glycol, PEG-200, PEG-400, and glycerol; from about 10% to about 50% a second solvent selected from the group consisting of ethanol, propanol and butanol; from about 0.01% to about 50% of a crosslinked copolymer of acrylic acid; from about 0% to about 3% of a neutralizing agent; and water.

27. A method for stimulating hair growth in a human comprising applying to human skin an effective amount of a 3, 7 or 3 and 7 thia or oxa prostanoic acid compound represented by the formula I

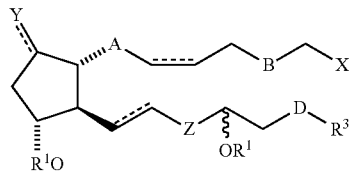

wherein hatched lines represent the α configuration, a triangle represents the β configuration and a dotted line represents the presence or absence of a double bond;
A and B are independently selected from the group consisting of O, S and $CH_2$;
provided that at least one of A or B is S;
D represents a covalent bond or $CH_2$, O, S or NH;
X is $CO_2R$, $CONR_2$, $CH_2OR$, $P(O)(OR)_2$, $CONRSO_2R$, $SONR_2$, tetrazole or triazole;
Y is O, halogen or cyano;
Z is $CH_2$ or a covalent bond;
R is H or $R^2$;
$R^1$ is H, $R^2$, or $COR^2$;
$R^2$ is $C_1$-$C_5$ lower alkyl or alkenyl and $R^3$ is hydrocarbyl or a substituted derivative thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in association with a pharmaceutical carrier adapted for topical application to mammalian skin.

28. The method of paragraph 27 wherein Y is O.

29. The method of paragraph 27 wherein the concentration of the compound applied is from about 0.0000001% to about 50% by weight of the pharmaceutical carrier.

30. The method of paragraph 27 wherein the compound is selected from the group consisting of:
{3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid methyl ester;
{3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid;
{3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid isopropyl ester;
{3-[(1R,2S,3R)-3-Hydroxy-2-((S)-(E)-3-hydroxy-5-(benzothienyl)pent-1-enyl)-5-oxocyclopentylsulfanyl] propylsulfanyl}acetic acid methyl ester;
{3-[(1R,2S,3R)-3-Hydroxy-2-((S)-(E)-3-hydroxy-5-(benzothienyl)pent-1-enyl)-5-oxocyclopentylsulfanyl] propylsulfanyl}acetic acid;
{3-[(1R,2S,3R)-3-Hydroxy-2-((S)-(E)-3-hydroxy-5-(benzothienyl)pent-1-enyl)-5-oxocyclopentylsulfanyl] propylsulfanyl}acetic acid isopropyl ester;
{3-[(1R,2S,3R)-3-Hydroxy-2-((S)-(E)-3-hydroxy-5-(benzofuranyl)pent-1-enyl)-5-oxocyclopentylsulfanyl] propylsulfanyl}acetic acid methyl ester;
{3-[(1R,2S,3R)-3-Hydroxy-2-((S)-(E)-3-hydroxy-5-(benzofuranyl)pent-1-enyl)-5-oxocyclopentylsulfanyl] propylsulfanyl}acetic acid; and
{3-[(1R,2S,3R)-3-Hydroxy-2-((S)-(E)-3-hydroxy-5-(benzofuranyl)pent-1-enyl)-5-oxocyclopentylsulfanyl] propylsulfanyl}acetic acid isopropyl ester.

31. The method of paragraph 27 wherein the compound is 3,7-dithia PGE1-isopropyl ester.

32. The method of paragraph 27 wherein the hair is eyelashes.

33. The method of paragraph 27 wherein the compound is applied to the eyelids.

34. The method of paragraph 33 wherein the compound is applied to the eyelid margins.

35. The method of paragraph 27 wherein the compound is applied to the eyebrows.

36. The method of paragraph 27 wherein the compound is applied to the scalp.

37. A method of increasing one or more of length, thickness, number, and density, of eyelash hair or eyebrow hair, comprising administering an effective amount of a 3, 7 or 3 and 7 thia or oxa protanoic acid compound represented by the formula I

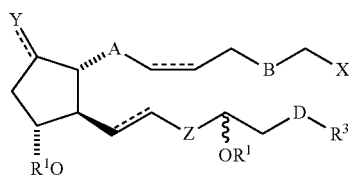

wherein hatched lines represent the α configuration, a triangle represents the β configuration and a dotted line represents the presence or absence of a double bond;

A and B are independently selected from the group consisting of O, S and $CH_2$;
provided that at least one of A or B is S;
D represents a covalent bond or $CH_2$, O, S or NH;
X is $CO_2R$, $CONR_2$, $CH_2OR$, $P(O)(OR)_2$, $CONRSO_2R$, $SONR_2$, tetrazole or triazole;
Y is O, halogen or cyano;
Z is $CH_2$ or a covalent bond;
R is H or $R^2$;
$R^1$ is H, $R^2$, or $COR^2$;
$R^2$ is $C_1$-$C_5$ lower alkyl or alkenyl and $R^3$ is hydrocarbyl or substituted derivatives thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in association with a pharmaceutical carrier adapted for topical application to mammalian skin, to a person on the area where hair growth is desired.

38. The method of paragraph 37 wherein Y is O.

39. The method of paragraph 37 wherein the composition is administered to an eyelid margin or to an eyebrow.

40. The method of claim 37 wherein the compound is selected from the group consisting of:
{3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid methyl ester;
{3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid;
{3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid isopropyl ester;
{3-[(1R,2S,3R)-3-Hydroxy-2-((S)-(E)-3-hydroxy-5-(benzothienyl)pent-1-enyl)-5-oxocyclopentylsulfanyl] propylsulfanyl}acetic acid methyl ester;
{3-[(1R,2S,3R)-3-Hydroxy-2-((S)-(E)-3-hydroxy-5-(benzothienyl)pent-1-enyl)-5-oxocyclopentylsulfanyl] propylsulfanyl}acetic acid;
{3-[(1R,2S,3R)-3-Hydroxy-2-((S)-(E)-3-hydroxy-5-(benzothienyl)pent-1-enyl)-5-oxocyclopentylsulfanyl] propylsulfanyl}acetic acid isopropyl ester;
{3-[(1R,2S,3R)-3-Hydroxy-2-((S)-(E)-3-hydroxy-5-(benzofuranyl)pent-1-enyl)-5-oxocyclopentylsulfanyl] propylsulfanyl}acetic acid methyl ester;
{3-[(1R,2S,3R)-3-Hydroxy-2-((S)-(E)-3-hydroxy-5-(benzofuranyl)pent-1-enyl)-5-oxocyclopentylsulfanyl] propylsulfanyl}acetic acid; and
{3-[(1R,2S,3R)-3-Hydroxy-2-((S)-(E)-3-hydroxy-5-(benzofuranyl)pent-1-enyl)-5-oxocyclopentylsulfanyl] propylsulfanyl}acetic acid isopropyl ester.

41. The method of paragraph 37 wherein the compound is 3,7-dithia PGE1-isopropyl ester.

42. The method of paragraph 37 wherein the hair is eyelashes.

43. The method of paragraph 37 wherein the compound is applied to the eyelids.

44. The method of paragraph 43 wherein the compound is applied to the eyelid margins.

45. The method of paragraph 37 wherein the compound is applied to the eyebrows.

46. The method of paragraph 37 wherein the compound is applied once a day.

47. A method for stimulating hair growth in a mammalian species or converting vellus hair or intermediate hair to terminal hair or stimulating hair follicles to increase hair growth and one or more properties selected from the group consisting of luster, sheen, brilliance, gloss, glow, shine or patina of hair associated with the follicles or increasing one or more of length, thickness, number, and density, of eyelash hair or eyebrow hair comprising applying to the skin of a patient an effective amount of an EP$_3$ agonist or an EP$_4$ agonist prodrug or a mixture thereof 48. The method of paragraph 47 comprising applying to the skin of a patient an effective amount of a 1 to 1 mixture of an EP$_3$ agonist and an EP$_4$ agonist prodrug.

49. A method of treating or preventing alopecia caused by chemotherapy which comprises applying to a patient in need thereof an effective amount of a 3, 7 or 3 and 7 thia or oxa

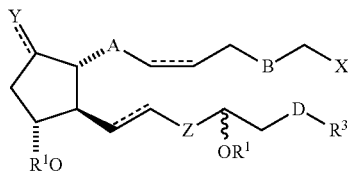

prostanoic acid compound represented by the formula I wherein hatched lines represent the α configuration, a triangle represents the β configuration and a dotted line represents the presence or absence of a double bond;

A and B are independently selected from the group consisting of O, S and CH$_2$;

provided that at least one of A or B is S;

D represents a covalent bond or CH$_2$, O, S or NH;

X is CO$_2$R, CONR$_2$, CH$_2$OR, P(O)(OR)$_2$, CONRSO$_2$R, SONR$_2$, tetrazole or triazole;

Y is O, halogen or cyano;

Z is CH$_2$ or a covalent bond;

R is H or R$^2$;

R$^1$ is H, R$^2$, or COR$^2$;

R$^2$ is C$_1$-C$_5$ lower alkyl or alkenyl and R$^3$ is hydrocarbyl or a substituted derivative thereof, wherein the substituents maybe selected from the group consisting of C$_1$-C$_5$ alkyl, halogen, CF$_3$, CN, NO$_2$, NR$_2$, CO$_2$R and OR in free form or a pharmaceutically acceptable salt thereof, in association with a pharmaceutical carrier adapted for topical application to mammalian skin.

50. The method of treating or preventing alopecia caused by chemotherapy according to claim 13 which comprises applying to a patient in need thereof an effective amount of a 3, 7 or

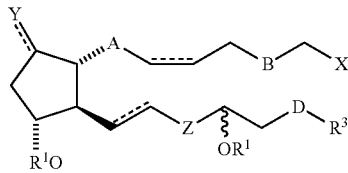

3 and 7 thia or oxa prostanoic acid compound represented by the formula I 3, 7 or 3 and 7 thia or oxa prostanoic acid compound represented by the formula I wherein hatched lines represent the α configuration, a triangle represents the β configuration and a dotted line represents the presence or absence of a double bond;

A and B are independently selected from the group consisting of O, S and CH$_2$;

provided that at least one of A or B is S;

D represents a covalent bond or CH$_2$, O, S or NH;

X is CO$_2$R, CONR$_2$, CH$_2$OR, P(O)(OR)$_2$, CONRSO$_2$R, SONR$_2$, tetrazole or triazole;

Y is O, halogen or cyano;

Z is CH$_2$ or a covalent bond;

R is H or R$^2$;

R$^1$ is H, R$^2$, or COR$^2$;

R$^2$ is C$_1$-C$_5$ lower alkyl or alkenyl and R$^3$ is hydrocarbyl or a substituted derivative thereof, wherein the substituents maybe selected from the group consisting of C$_1$-C$_5$ alkyl, halogen, CF$_3$, CN, NO$_2$, NR$_2$, CO$_2$R and OR in free form or a pharmaceutically acceptable salt thereof, as a foam produced from a foamable liquid composition, wherein said foamable liquid composition comprises one or more of said compounds of formula I, a surfactant, wherein the surfactant optionally includes a foam stabilizer and an aqueous-alcohol solvent, comprising water and an alcohol, which solvent enables said compound to be solubilized.

51. A foamable liquid composition, for use in the method of claim 1, comprising one or more of the a 3, 7 or 3 and 7 thia or oxa prostanoic acid compounds represented by the formula

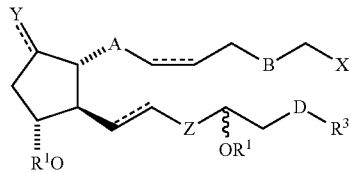

wherein hatched lines represent the α configuration, a triangle represents the β configuration and a dotted line represents the presence or absence of a double bond;

A and B are independently selected from the group consisting of O, S and CH$_2$;

provided that at least one of A or B is S;

D represents a covalent bond or CH$_2$, O, S or NH;

X is CO$_2$R, CONR$_2$, CH$_2$OR, P(O)(OR)$_2$, CONRSO$_2$R, SONR$_2$, tetrazole or triazole;

Y is O, halogen or cyano;

Z is CH$_2$ or a covalent bond;

R is H or R$^2$;

R$^1$ is H, R$^2$, or COR$^2$;

R$^2$ is C$_1$-C$_5$ lower alkyl or alkenyl and R$^3$ is hydrocarbyl or a substituted derivative thereof, wherein the substituents maybe selected from the group consisting of C$_1$-C$_5$ alkyl, halogen, CF$_3$, CN, NO$_2$, NR$_2$, CO$_2$R and OR in free form or a pharmaceutically acceptable salt thereof, and a surfactant, wherein the surfactant optionally includes a foam stabilizer and an aqueous-alcohol solvent, comprising water and an alcohol, which solvent enables said compound to be solubilized.

52. The composition of paragraph 51 wherein said aqueous-alcohol solvent further comprises an acid and a water soluble solvent, wherein said acid is an inorganic acid, or an organic acid containing eight carbons or less and said water soluble solvent is selected from the group consisting of butylene glycol, glycerin, polyglycerin, ethylene glycol, and propylene glycol and said alcohol is selected from the group consisting of methanol, ethanol, propanol and mixtures thereof.

53. A gel comprising a 3, 7 or 3 and 7 thia or oxa prostanoic acid compound represented by the formula I

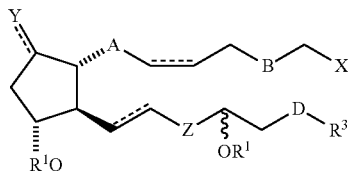

wherein hatched lines represent the α configuration, a triangle represents the β configuration and a dotted line represents the presence or absence of a double bond;

A and B are independently selected from the group consisting of O, S and $CH_2$;

provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$, tetrazole or triazole;

Y is O, halogen or cyano;

Z is $CH_2$ or a covalent bond;

R is H or $R^2$;

$R^1$ is H, $R^2$, or $COR^2$;

$R^2$ is $C_1$-$C_5$ lower alkyl or alkenyl and $R^3$ is hydrocarbyl or a substituted derivative thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in a pharmaceutically-acceptable solvent, comprising propylene glycol and alcohol and a crosslinked acrylic polymer thickening agent such as a Carbomer, e.g. Carbomer 934P, wherein the crosslinked acrylic polymer thickening agent is neutralized with a neutralizing agent such as diisopropanolamine.

54. A composition in the form of a gel comprising a 3, 7 or 3 and 7 thia or oxa prostanoic acid compound represented by the formula I

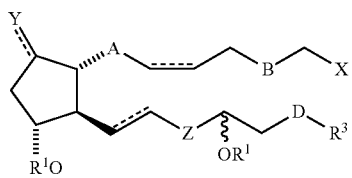

wherein hatched lines represent the α configuration, a triangle represents the β configuration and a dotted line represents the presence or absence of a double bond;

A and B are independently selected from the group consisting of O, S and $CH_2$;

provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$, tetrazole or triazole;

Y is O, halogen or cyano;

Z is $CH_2$ or a covalent bond;

R is H or $R^2$;

$R^1$ is H, $R^2$, or $COR^2$;

$R^2$ is $C_1$-$C_5$ lower alkyl or alkenyl and $R^3$ is hydrocarbyl or a substituted derivative thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, a crosslinked copolymer of acrylic acid as a thickening agent, and a pharmaceutically acceptable solvent.

55. The composition of paragraph 54, wherein said pharmaceutically acceptable solvent is selected from the group consisting of ethanol, propanol, butanol, propylene glycol, dipropylene glycol, hexylene glycol, 1,3-butylene glycol, PEG-200, PEG-400, glycerol and mixtures thereof.

56. A composition in the form of a gel comprising: from about 0.1 to 10% of a 3, 7 or 3 and 7 thia or oxa prostanoic acid compound represented by the formula I

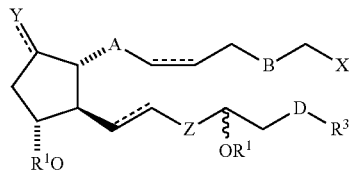

wherein hatched lines represent the α configuration, a triangle represents the β configuration and a dotted line represents the presence or absence of a double bond;

A and B are independently selected from the group consisting of O, S and $CH_2$;

provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$, tetrazole or triazole;

Y is O, halogen or cyano;

Z is $CH_2$ or a covalent bond;

R is H or $R^2$;

$R^1$ is H, $R^2$, or $COR^2$;

$R^2$ is $C_1$-$C_5$ lower alkyl or alkenyl and $R^3$ is hydrocarbyl or a substituted derivative thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof from about 30% to about 80% of a first solvent selected from the group consisting of propylene glycol, dipropylene glycol, hexylene glycol, 1,3-butylene glycol, PEG-200, PEG-400, and glycerol; from about 10% to about 50% a second solvent selected from the group consisting of ethanol, propanol and butanol; from about 0.01% to about 50% of a crosslinked copolymer of acrylic acid; from about 0% to about 3% of a neutralizing agent and water.

These and other aspects of the invention will become apparent from the description of the invention which follows below.

DETAILED DESCRIPTION OF THE PREFERRED EMBODIMENT

Alopecia (baldness) a deficiency of either normal or abnormal hair, is primarily a cosmetic problem in humans. It is a deficiency of terminal hair, the broad diameter, colored hair that is readily seen. However, in the so-called bald person although there is a noticeable absence of terminal hair, the skin does contain vellus hair which is a fine colorless hair which may require microscopic examination to determine its presence. This vellus hair is a precursor to terminal hair. In accordance with the invention as described herein, compounds represented by formula I:

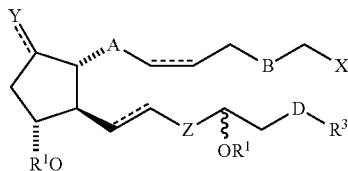

wherein hatched lines represent the α configuration, a triangle represents the β configuration and a dotted line represents the presence or absence of a double bond;

A and B are independently selected from the group consisting of O, S and $CH_2$;

provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$ or

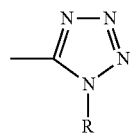

Y is O, halogen or cyano;

Z is $CH_2$ or a covalent bond;

R is H or $R^2$;

$R^1$ is H, $R^2$, phenyl, or $COR^2$;

$R^2$ is $C_1$-$C_5$ lower alkyl or alkenyl and $R^3$ is hydrocarbyl, or substituted derivatives thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in association with a pharmaceutical carrier adapted for topical application to mammalian skin.

Some examples of representative compounds useful in the practice of the present invention include the compounds shown in Table 1:

TABLE 1

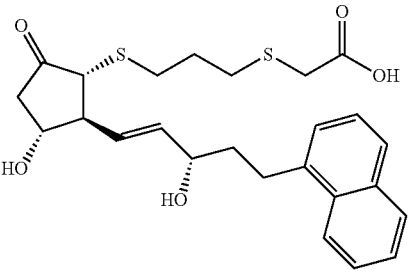 [SMILES: O=C(O)CSCCCS[C@H]1C(=O)C[C@@H](O)[C@@H]1/C=C/[C@@H](O)CCc1cccc2ccccc12]

{3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid methyl ester.

TABLE 1-continued

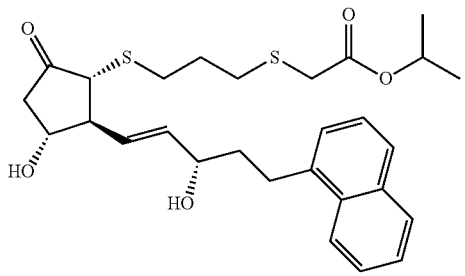 [SMILES: CC(C)OC(=O)CSCCCS[C@H]1C(=O)C[C@@H](O)[C@@H]1/C=C/[C@@H](O)CCc1cccc2ccccc12]

{3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid.

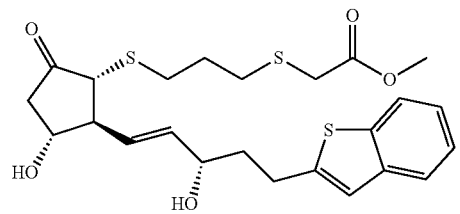

{3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid isopropyl ester.

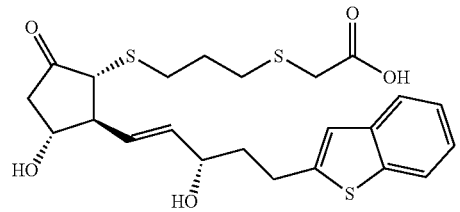 [SMILES: O=C(O)CSCCCS[C@H]1C(=O)C[C@@H](O)[C@@H]1/C=C/[C@@H](O)CCc1cc2ccccc2s1]

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid methyl ester.

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid.

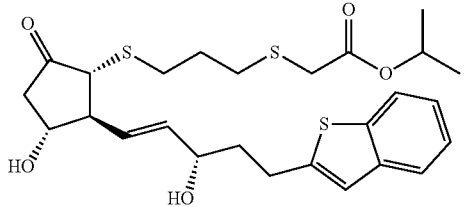 [SMILES: CC(C)OC(=O)CSCCCS[C@H]1C(=O)C[C@@H](O)[C@@H]1/C=C/[C@@H](O)CCc1cc2ccccc2s1]

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid isopropyl ester.

TABLE 1-continued

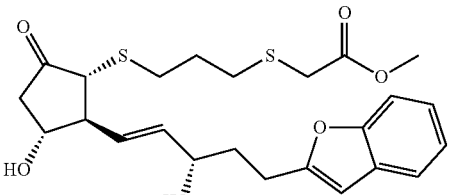

{3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid methyl ester.

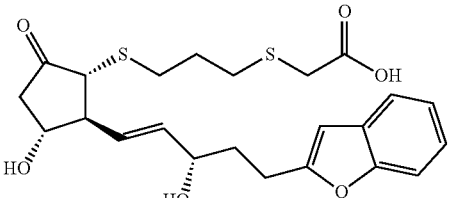

{3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid.

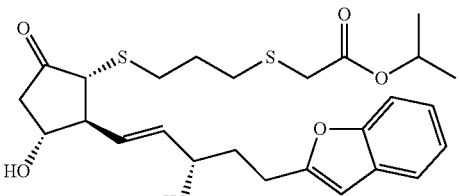

{3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid isopropyl ester.

Presently preferred compounds for use in the practice of the present invention are {3-[(1R,2S,3R)-3-Hydroxy-2-((S)-(E)-3-hydroxyoct-1-enyl)-5-oxocyclopentyl-sulfanyl]propylsulfanyl}acetic acid (3,7-dithia PGE1) and {3-[(1R,2S,3R)-3-Hydroxy-2-((S)-(E)-3-hydroxyoct-1-enyl)-5-oxocyclopentyl-sulfanyl]propylsulfanyl}acetic acid isopropyl ester (3,7-dithia PGE1-isopropyl ester).

The synthesis of the compounds described above has been disclosed in U.S. Pat. Nos. 6,410,591; 6,538,018: 6,767,920 and 6,956,057 which are hereby incorporated by reference in their entireties. The invention thus relates to the use of the above compounds, or prodrugs of the active compounds, for treatment for the stimulation of hair growth. As used herein, hair growth includes hair associated with the scalp, eyebrows, eyelids (including upper and lower eyelid margins), beard, and other areas of the skin of animals including humans.

In accordance with one aspect of the invention, the compound is mixed with a dermatologically compatible vehicle or carrier. The vehicle which may be employed for preparing compositions of this invention may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to dermatological compositions for topical treatment for the stimulation of hair growth which comprise an effective hair growth stimulating amount of one or more compounds as defined above and a dermatologically compatible carrier. Effective amounts of the active compounds may be determined by one of ordinary skill in the art but will vary depending on the compound employed, frequency of application and desired result, and the compound will generally range from about 0.0000001 to about 50%, by weight, of the dermatological composition, preferably from about 0.001 to about 50%, by weight, of total dermatological composition, more preferably from about 0.1 to about 30%, by weight of the composition and most preferably from 0.1, 0.2, 0.3, 0.4. 0.5, 0.6, 0.7, 0.8, 0.9 to 1.0% by weight of the composition.

The present invention finds application in all mammalian species, including both humans and animals. In humans, the compounds of the subject invention can be applied for example, to the scalp, face, beard, head, pubic area, upper lip, eyebrows, and eyelids. In animals raised for their pelts, e.g., mink, the compounds can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated by this invention include pharmaceutical compositions suited for topical and local action.

The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin surface to be treated. Conventional pharmaceutical forms for this purpose include ointments, liniments, creams, shampoos, lotions, pastes, jellies, sprays, aerosols, gels, foams and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds are applied repeatedly for a sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably at least six months.

For topical use on the eyelids or eyebrows, the active compounds can be formulated in aqueous solutions, creams, ointments or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid etc. as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels. Depending on the actual formulation and compound to be used, various amounts of the drug and different dose regimens may be employed. Typically, the daily amount of compound for treatment of the eyelid may be about 0.1 ng to about 100 mg per eyelid.

For topical use on the skin and the scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

In instances wherein it is desirable to maximize the contact of the active ingredients, disclosed above, with the skin of a patient, the formulation of the pharmaceutical composition of the invention may be in the form of a foam or gel. A foam is especially preferred for treating the scalp to restore lost hair or prevent hair loss, including loss of the scalp hair or eyelashes or eyebrows, resulting from chemotherapy.

A foamable liquid composition, for use in the method of this invention, comprises one or more of the above compounds of formula I, and one or more of: a surfactant, wherein the surfactant optionally includes a foam stabilizer; a solvent, such as water; an alcohol; an acid and a water soluble solvent.

In one example, the solvent includes an acid at a concentration of from 0.5 to 5 percent, by weight, of the foamable liquid composition. The acid is optionally any inorganic acid or any organic acid with chain length of eight carbons or less. A preferred composition of the solvent includes from 1 to 4 percent, by weight, lactic acid, from 1 to 50, preferably from 5 to 30 percent, by weight, of an alcohol having from one to four carbon atoms, such as methanol, ethanol, propanol and mixtures thereof, and one or more water soluble solvents, such as butylene glycol, glycerin, polyglycerin, ethylene glycol, and propylene glycol. Preferably said alcohol is ethanol and preferably said water soluble solvent is propylene glycol in an amount of from 1 to 20 percent, by weight, and more preferably from 5 to 15 percent, by weight, of the foamable liquid composition.

A pharmaceutically elegant gel comprising the compounds of formula I may be prepared by mixing the below-described mixtures:

| Ingredient | % w/w |
|---|---|
| Part I | |
| Purified water USP | q.s. 100 |
| Carbopol ® 934P | 0.45 |
| Part II | |
| Ompound of formula | 0.01 to 10.0 |
| propylene glycol USP | 10 |
| alcohol USP | 13 |
| diisopropanolamine NF | 0.45 |
| Part III | |
| alcohol USP | 27 |

The component parts are prepared separately. Part III is then mixed with Part I. When a uniform mixture is obtained, Part II is then added using planetary mixing under vacuum until a uniform gel is obtained.

The invention is further illustrated by the following non-limiting examples:

Example 1

In Vivo Treatment

A study will be initiated to systematically evaluate the appearance of lashes and hair around the eyes of patients who are administering the drug, i.e. {3-[(1R,2S,3R)-3-Hydroxy-2-((S)-(E)-3-hydroxyoct-1-enyl)-5-oxocyclopentyl-sulfanyl]propylsulfanyl}acetic acid (3,7-dithia PGE1), or {3-[(1R,2S,3R)-3-Hydroxy-2-((S)-(E)-3-hydroxyoct-1-enyl)-5-oxocyclopentyl-sulfanyl]propylsulfanyl}acetic acid isopropyl ester (3,7-dithia PGE1-isopropyl ester) {3-[(1R,2S,3R)-3-Hydroxy-2-((S)-(E)-3-hydroxyoct-1-enyl)-5-oxocyclopentyl-sulfanyl]propylsulfanyl}acetic acid (3,7-dithia PGE1), or {3-[(1R,2S,3R)-3-Hydroxy-2-((S)-(E)-3-hydroxyoct-1-enyl)-5-oxocyclopentyl-sulfanyl]propylsulfanyl}acetic acid isopropyl ester (3,7-dithia PGE1-isopropyl ester) or combinations thereof in only one eye. Each subject is treated daily by the topical application of one drop of one of the compounds at a dosage of 1.5 .mu.g/ml/eye/day (0.03%, by weight,) to the eyelid margin by instilling the drop onto the upper eyelid margin. The non-treated eye will serve as a control.

Observations will be made under high magnification at the slit lamp biomicroscope. Documentation of differences between the control and treatment areas will be accomplished using a camera specially adapted for use with the slit lamp biomicroscope.

The results of the observations will be as follows:

Length of lashes: Increased length of eyelashes will be regularly observed on the side treated with drug. The difference in length varies from approximately 10% to as much as 30%.

Number of lashes: Increased numbers of lashes will be observed in the treated eye of each patient. In areas where there are a large number of lashes in the control eye, the increased number of lashes in the drug-treated eye will give the lashes on the treated side a more thickly matted overall appearance.

Auxiliary lash-like hair growth: Several patients will have an apparent increase in lash-like hair in transitional areas adjacent to areas of normal lash distribution. These prominent lash-like hairs appear to be of comparable length to the actual lashes. These long, thick lash-like hairs will be present in the central portion of the lids of several patients in a linear arrangement just above the lash line. Hairs will be present at similar locations in the control eyes but by contrast will be thinner or more fine in appearance, have less luster and pigment and are more flat against the skin of the lid typical of vellus or intermediate hairs. In several patients, lash-like terminal hairs will grow luxuriantly in the medial canthal area in the treated eye. In the corresponding control eye, vellus hairs will be seen at the same location. Lash-like hairs will be present in the lateral canthal area of the treated eye but not in the control eye in several subjects.

Increased growth of vellus hair on lids: Fine microscopic vellus hair will be present on the skin of the lids and will be easily seen with the slit lamp biomicroscope. This vellus hair will be typically denser adjacent to and below the lateral portion of the lower lids. While remaining microscopic, vellus hairs will increase in number, appear more robust and are much longer and thicker in treated than in control eyes in the areas below and lateral to the lower lid.

Perpendicular angulation of hairs: In areas where there are lash-like hairs above the lash line and in the medial and lateral canthal areas, the hairs will be much longer, thicker and heavier.

The above compounds are evaluated for their selectivity for various prostaglandin (PG) receptors. The results are reported in Table 2, and show that they are selective for $EP_3$ and $EP_4$ receptors. Thus, the method of the present invention may be carried out with $EP_3$ and $EP_4$ receptor agonists and/or pro-drugs of $EP_3$ and $EP_4$ receptor agonists.

TABLE 2

| | EC50 (nM) on Prostanoid Receptor Functional Activity Measured by FLIPR | | | | | | | |
|---|---|---|---|---|---|---|---|---|
| | hDP | $hEP_1$ | $hEP_2$ | $hEP_3$ | $hEP_4$ | hFP | hIP | hTP | |
| #1 | >10,000 | 304 | 380 | 36 | 0.26 | >10,000 | >10,000 | 561 | n = 6 |
| #2 | >10,000 | 2258 | 1106 | 44 | 2.55 | >10,000 | >10,000 | 3287 | n = 3 |

Example 2

Topical Cream

A topical cream is prepared as follows: Tegacid and spermaceti are melted together at a temperature of 70-80° C. Methylparaben is dissolved in about 500 gm of water and propylene glycol, polysorbate 80, and 1 to 1 mixture of 3,7-dithia PGE1 and 3,7-dithia PGE1-isopropyl ester are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

Example 3

Topical Cream

A topical cream is prepared as follows: Tegacid and spermaceti are melted together at a temperature of 70-80° C. Methylparaben is dissolved in water and propylene glycol, polysorbate 80, and a 1 to 1 mixture of 3,7-dithia PGE1 and 3,7-dithia PGE1-isopropyl ester are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed. The composition will be applied to bald human scalp once daily to stimulate the growth of hair.

Example 4

Topical Ointment

An ointment containing 2% by weight a 1 to 1 mixture of 3,7-dithia PGE1 and 3,7-dithia PGE1-isopropyl ester is prepared as follows:

White petrolatum and wool fat are melted, strained and liquid petrolatum is added thereto. The mixture of 3,7-dithia PGE1 and 3,7-dithia PGE1-isopropyl ester, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

The foregoing ointment can be applied topically to mammalian skin for increased rate of hair growth, and can be prepared by omitting the zinc oxide and calamine.

Example 5

Ointment

A dermatological ophthalmic ointment containing 10% by weight a 1 to 1 mixture of 3,7-dithia PGE1 and 3,7-dithia PGE1-isopropyl ester is prepared by adding the active compound to light liquid petrolatum. White petrolatum is melted together with wool fat, strained, and the temperature adjusted to 45-50° C. The liquid petrolatum slurry is added and the ointment stirred until congealed. Suitably the ointment is packaged in 30 gm tubes.

The foregoing ointment can be applied to the eyelid to enhance the growth of eyelashes. Similarly the composition can be applied to the brow for eyebrow growth.

Example 6

Solution

An aqueous solution containing 5%, by weight, a 1 to 1 mixture of 3,7-dithia PGE1 and 3,7-dithia PGE1-isopropyl ester is prepared as follows. A mixture of 3,7-dithia PGE1 and 3,7-dithia PGE1-isopropyl ester is dissolved in water and the resulting solution is sterilized by filtration. The solution is aseptically filled into sterile containers.

The composition so prepared can be used in the topical treatment of baldness by application to the scalp daily.

Example 7

Lotion

A sample of a 1 to 1 mixture of 3,7-dithia PGE1 and 3,7-dithia PGE1-isopropyl ester is dissolved in the vehicle of N-methylpyrrolidone and propylene glycol. The composition can be used for application to dogs or cats having hair loss due to mange or alopecia of other causes.

Example 8

Aerosol

An aerosol containing approximately 0.1% by weight a 1 to 1 mixture of 3,7-dithia PGE1 and 3,7-dithia PGE1-isopropyl ester is prepared by dissolving a 1 to 1 mixture of 3,7-dithia PGE1 and 3,7-dithia PGE1-isopropyl ester in absolute alcohol. The resulting solution filtered to remove particles and lint. This solution is chilled to about minus 30° C. To the solution is added a chilled mixture of dichlorodifluoromethane and dichlorotetrafluoroethane. Thirteen ml plastic-coated amber bottles are cold filled with 11.5 gm each of the resulting solution and capped. The composition can be sprayed on the scalp daily to stimulate the growth of hair.

Example 9

Dusting Powder

A powder of the compound a 1 to 1 mixture of 3,7-dithia PGE1 and 3,7-dithia PGE1-isopropyl ester is prepared by mixing in dry form with talcum powder at a weight/weight ratio of 1:10. The powdered mixture is dusted on the fur of minks or other commercially valuable fur bearing animals and show animals for increased rate of hair growth.

Example 10

Related Compounds

Following the procedure of the preceding Examples, compositions are similarly prepared substituting an equimolar amount of a compound of Formula I for the 1 to 1 mixture of 3,7-dithia PGE1 and 3,7-dithia PGE1-isopropyl ester disclosed in the preceding Examples similar results are obtained.

Example 11

In-Vivo Animal Studies

A comparison of a topical composition comprising 0.03%, by weight, of [(1R,3R)-3-hydroxy-2-[(1E,3S)-3-hydroxyoct-1-en-1-yl]-5-oxocyclopentyl sulfanyl]propylsulfanyl}acetic acid or (3,7-dithia PGE1-isopropyl ester) with the vehicle, for the onset of hair growth and full hair growth, in a mouse model for hair growth, gave the results summarized in Table 3, below.

TABLE 3

First Day of New Hair Appearance and Hair grow back normal

| Group | Test Article | Animal Number | First day of new hair appearance (Day) | First day of hair grow back to normal (Day) |
|---|---|---|---|---|
| 1 | PDA 206 | 101 | 14 | 28 |
|  | (0.03% 3,7- | 102 | 26 | 52 |
|  | dithia PGE2 | 103 | 21 | 52 |
|  | isopropyl ester) | 104 | 18 | N.O. |
|  |  | 105 | 16 | 31 |
|  |  | 106 | 14 | 25 |
|  |  | 107 | 14 | 35 |
|  |  | 108 | 14 | 26 |
|  |  | Mean | 17.13 | 35.57 |
|  |  | SD | 4.39 | 11.70 |
| 2 | PDA 210 | 201 | 31 | 47 |
|  | (Vehicle) | 202 | 14 | N.O. |
|  |  | 203 | 22 | 40 |
|  |  | 204 | 13 | 21 |
|  |  | 205 | 14 | 27 |
|  |  | 206 | 18 | 47 |
|  |  | 207 | 31 | 48 |
|  |  | 208 | 42 | 55 |
|  |  | Mean | 23.13 | 40.71 |
|  |  | SD | 10.53 | 12.34 |

The results of this comparison shows that a representative compound used in the method of treatment of this invention significantly improves the onset of hair growth and the return to normal. This result further indicates that the compounds are useful in treating alopecia caused by chemotherapy.

Example 12

Foam

A liquid composition for the treatment and prevention of hair loss in humans, said liquid comprising: a foamable composition, comprising. 0.03%, by weight, of a compound of formula I, e.g. [(1R,3R)-3-hydroxy-2-[(1E,3S)-3-hydroxyoct-1-en-1-yl]-5-oxocyclopentyl sulfanyl]propylsulfanyl}acetic acid or (3,7-dithia PGE1-isopropyl ester) dissolved in a solvent system, comprising an aqueous-alcoholic solvent medium; a surfactant, selected from the group consisting of: an anionic surfactant; a cationic surfactant; a non-ionic surfactant; an amphoteric surfactant and mixtures thereof and a foam stabilizer, said foam stabilizer, selected from the group consisting of: a fatty amine oxide; a quaternary amine; a derivative of cellulose; a methyl cellulose derivative; and an ethyl cellulose derivative is prepared by methods known in the art. The foamable composition has a hydrophilic-lipophilic balance (HLB) value of greater than fifteen.

Said composition comprises from 0.1 to 5 percent of a surfactant, preferably oleth-20, by weight, and from 0.05 to 0.5 percent of a foam stabilizer, e.g. lauryl glucoside, by weight.

Said solvent system comprises water; an acid, wherein said acid is selected from the group consisting of: an inorganic acid; and an organic acid comprising eight or fewer carbon atoms, e.g. lactic acid, and an alcohol comprising one to four carbon atoms.

Said alcohol is selected from the group consisting of methanol, ethanol, propanol and mixtures thereof.

Said solvent system further comprises at least one of butylene glycol, glycerin, polyglycerin, ethylene glycol and propylene glycol.

The foamable liquid composition includes from 30 to 80 percent water, by weight. Preferably the foamable liquid composition includes from 30 to 60 percent water, by weight. The foamable liquid composition includes an acid at a concentration of from 0.5 to 5 percent, by weight, of the foamable liquid composition, preferably from 1 to 4 percent, by weight, lactic acid; from 1 to 50, preferably from 5 to 30 percent, by weight, of an alcohol having from one to four carbon atoms, such as methanol, ethanol, propanol and mixtures thereof, and one or more water soluble solvents, such as butylene glycol, glycerin, polyglycerin, ethylene glycol, and propylene glycol. Preferably said alcohol is ethanol and preferably said water soluble solvent is propylene glycol in an amount of from 1 to 20 percent, by weight, and more preferably from 5 to 15 percent, by weight, of the foamable liquid composition.

Said foam is utilized by a method of delivering said composition as a foam for the treatment and prevention of hair loss in humans, said method comprising the steps of: providing said foamable composition in a container, producing a foam from said foamable liquid composition and dispensing a measured dosage of said foam from said container onto a patient.

Said step of producing a foam may comprise a step of: mixing said foamable composition and air contained within said container.

Said foam is administered to the scalp or other body part of a patient and is maintained thereon for a time sufficient to obtain the desired therapeutic effect.

Example 13

Gel

A pharmaceutically elegant gel comprising 0.03%, by weight, of a compound of formula I, e.g. [(1R,3R)-3-hydroxy-2-[(1E,3S)-3-hydroxyoct-1-en-1-yl]-5-oxocyclopentyl sulfanyl]propylsulfanyl}acetic acid or (3,7-dithia PGE1- isopropyl ester and alcohol and a crosslinked acrylic polymer thickening agent such as a Carbomer, e.g. Carbomer 934P, is prepared as described below.

The crosslinked acrylic polymer thickening agent is neutralized with a neutralizing agent such as diisopropanolamine.

The gel comprises from 0.001% to 10% (3,7-dithia PGE1-isopropyl ester) by weight. More preferably said gel comprises from 0.01% to 0.5% (3,7-dithia PGE1-isopropyl ester), by weight, most preferably said composition comprises 0.3%, by weight Said pharmaceutically acceptable solvent is selected from the group consisting of ethanol, propanol, butanol, propylene glycol, dipropylene glycol, hexylene glycol, 1,3-butylene glycol, PEG-200, PEG-400, glycerol and mixtures thereof.

Most preferably, said solvent is selected from the group consisting of ethanol and isopropanol.

Alternatively, said solvent selected from the group consisting of propylene glycol, dipropylene glycol, hexylene glycol, 1,3-butylene glycol, PEG-200, PEG-400, and glycerol.

Most preferably, said solvent is propylene glycol.

In a second alternative embodiment of the invention, said solvent comprises a mixture comprising a first solvent selected from the group consisting of ethanol, propanol and butanol and a second solvent selected from the group consisting of propylene glycol, dipropylene glycol, hexylene glycol, 1,3-butylene glycol, PEG-200, PEG-400, and glycerol.

Preferably, in said second alternative embodiment of the invention, said solvent comprises a mixture of ethanol and propylene glycol.

The gel further comprising a neutralizing agent, wherein said neutralizing agent may be selected from the group consisting of ammonium hydroxide, arginine, 2-amino-2-methyl-1-propanol, dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, aminomethylpropanol, sodium hydroxide, and potassium hydroxide.

The component parts are prepared separately. Part III is then mixed with Part I. When a uniform mixture is obtained, Part II is then added using planetary mixing under vacuum until a uniform gel is obtained.

| Ingredient | % w/w |
|---|---|
| Part I | |
| Purified water USP | q.s. 100 |
| Carbopol ® 934P | 0.45 |
| Part II | |
| (3,7-dithia PGE1-isopropyl ester) | 0.3 |
| propylene glycol USP | 10 |
| alcohol USP | 13 |
| diisopropanolamine NF | 0.45 |
| Part III | |
| alcohol USP | 27 |

The component parts are prepared separately. Part III is then mixed with Part I. When a uniform mixture is obtained, Part II is then added using planetary mixing under vacuum until a uniform gel is obtained.

While the preferred embodiment of the invention has been illustrated and described, it will be appreciated that various changes can be made therein without departing from the spirit and scope of the invention. For example, while the above examples demonstrates the use of {3-[(1R,2S,3R)-3-Hydroxy-2-((S)-(E)-3-hydroxyoct-1-enyl)-5-oxocyclopentyl-sulfanyl]propylsulfanyl}acetic acid (3,7-dithia PGE1), {3-[(1R,2S,3R)-3-Hydroxy-2-((S)-(E)-3-hydroxyoct-1-enyl)-5-oxocyclopentyl-sulfanyl]propylsulfanyl}acetic acid isopropyl ester (3,7-dithia PGE1-isopropyl ester) and a 50/50 mixture thereof in the method of the present invention, these compounds demonstrate that the combination of an EP$_4$ agonist prodrug with an EP$_3$ agonist is effective in a method for stimulating hair growth in a mammalian species comprising the application to mammalian skin of an effective amount of said combination.

The invention claimed is:

1. A method for stimulating hair growth in a human comprising applying to human skin an effective amount of a 3, 7 or 3 and 7 thia or oxa prostanoic acid compound represented by the formula I

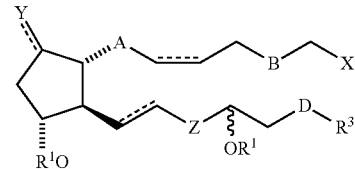

wherein hatched lines represent the α configuration, a triangle represents the β configuration and a dotted line represents the presence or absence of a double bond;

A and B are independently selected from the group consisting of O, S and CH$_2$;
provided that at least one of A or B is S;
D represents a covalent bond or CH$_2$, O, S or NH;
X is CO$_2$R, CONR$_2$, CH$_2$OR, P(O)(OR)$_2$, CONRSO$_2$R, SONR$_2$, tetrazole or triazole;
Y is O, halogen or cyano;
Z is CH$_2$ or a covalent bond;
R is H or R$^2$;
R$^1$ is H, R$^2$, or COR$^2$; and,
R$^2$ is C$_1$-C$_5$ lower alkyl or alkenyl and R$^3$ is hydrocarbyl or a substituted derivative thereof, wherein the substituents maybe selected from the group consisting of C$_1$-C$_5$ alkyl, halogen, CF$_3$, CN, NO$_2$, NR$_2$, CO$_2$R and OR in free form or a pharmaceutically acceptable salt thereof, in association with a pharmaceutical carrier adapted for topical application to mammalian skin.

2. The method of claim 1 wherein Y is O.

3. The method of claim 2 wherein the concentration of the compound applied is from about 0.0000001% to about 50% by weight of the pharmaceutical carrier.

4. The method of claim 1 wherein the compound is selected from the group consisting of:
3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid methyl ester;
{3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid;
{3-[(1R,2S,3R)-3-Hydroxy-2-((S)-(E)-3-(hydroxy)-5-(naphthyl)pent-1-enyl)-5-oxocyclopentylsulfanyl] propylsulfanyl}acetic acid isopropyl ester;

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid methyl ester;

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid;

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid isopropyl ester;

{3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid methyl ester;

{3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid; and {3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid isopropyl ester.

5. The method of claim 1 wherein the compound is 3,7-dithia PGE1-isopropyl ester.

6. The method of claim 1 wherein the hair is eyelashes.

7. The method of claim 1 wherein the compound is applied to the eyelids.

8. The method of claim 7 wherein the compound is applied to the eyelid margins.

9. The method of claim 1 wherein the compound is applied to the eyebrows.

10. The method of claim 1 wherein the compound is applied to the scalp.

11. A method of increasing one or more of length, thickness, number, and density, of eyelash hair or eyebrow hair, comprising administering an effective amount of a 3, 7 or 3 and 7 thia or oxa protanoic acid compound represented by the formula I

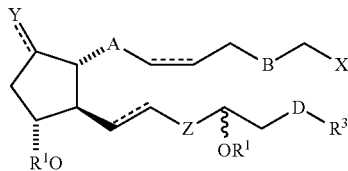

wherein hatched lines represent the α configuration, a triangle represents the β configuration and a dotted line represents the presence or absence of a double bond;
A and B are independently selected from the group consisting of O, S and $CH_2$;
provided that at least one of A or B is S;
D represents a covalent bond or $CH_2$, O, S or NH;
X is $CO_2R$, $CONR_2$, $CH_2OR$, $P(O)(OR)_2$, $CONRSO_2R$, $SONR_2$, tetrazole or triazole;
Y is O, halogen or cyano;
Z is $CH_2$ or a covalent bond;
R is H or $R^2$;
$R^1$ is H, $R^2$, or $COR^2$;
$R^2$ is $C_1$-$C_5$ lower alkyl or alkenyl and $R^3$ is hydrocarbyl or substituted derivatives thereof, wherein the substituents maybe selected from the group consisting of $C_1$-$C_5$ alkyl, halogen, $CF_3$, CN, $NO_2$, $NR_2$, $CO_2R$ and OR in free form or a pharmaceutically acceptable salt thereof, in association with a pharmaceutical carrier adapted for topical application to mammalian skin, to a person on the area where hair growth is desired.

12. The method of claim 11 wherein Y is O.

13. The method of claim 11 wherein the composition is administered to an eyelid margin or to an eyebrow.

14. The method of claim 11 wherein the compound is selected from the group consisting of:

3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid methyl ester;

{3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid;

{3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid isopropyl ester;

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid methyl ester;

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid;

{3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid isopropyl ester;

{3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid methyl ester;

{3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid; and {3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid isopropyl ester.

15. The method of claim 11 wherein the compound is 3,7-dithia PGE1-isopropyl ester.

16. The method of claim 11 wherein the hair is eyelashes.

17. The method of claim 11 wherein the compound is applied to the eyelids.

18. The method of claim 17 wherein the compound is applied to the eyelid margins.

19. The method of claim 11 wherein the compound is applied to the eyebrows.

20. The method of claim 11 wherein the compound is applied once a day.

* * * * *

UNITED STATES PATENT AND TRADEMARK OFFICE
CERTIFICATE OF CORRECTION

| | | |
|---|---|---|
| PATENT NO. | : 8,859,616 B2 | |
| APPLICATION NO. | : 13/354479 | |
| DATED | : October 14, 2014 | |
| INVENTOR(S) | : Jenny W. Wang et al. | |

It is certified that error appears in the above-identified patent and that said Letters Patent is hereby corrected as shown below:

On the title page, in item (56), in column 2, under "Other Publications", line 7, delete "Chemisty" and insert -- Chemistry --, therefor.

On title page 2, in item (56), in column 2, under "Other Publications", line 11, delete "Acclerants" and insert -- Accelerants --, therefor.

On title page 3, in item (56), in column 2, under "Other Publications", line 53, delete "Ostroblastic" and insert -- Osteoblastic --, therefor.

On title page 4, in item (56), in column 1, under "Other Publications", line 63, delete "Opthalmology," and insert -- Ophthalmology, --, therefor.

On title page 4, in item (56), in column 2, under "Other Publications", line 58, delete "Dellivery" and insert -- Delivery --, therefor.

On title page 5, in item (56), in column 1, under "Other Publications", line 36, delete "Opthalmol." and insert -- Ophthalmol., --, therefor.

On title page 5, in item (56), in column 1, under "Other Publications", line 52, delete "Immunodulatory" and insert -- Immunomodulatory --, therefor.

On title page 5, in item (56), in column 2, under "Other Publications", line 3, delete "Opthalmol." and insert -- Ophthalmol., --, therefor.

On title page 5, in item (56), in column 2, under "Other Publications", line 5, delete "Ozagrel-HCI" and insert -- Ozagrel-HCl --, therefor.

On title page 6, in item (56), in column 1, under "Other Publications", line 24, delete "Lipopolysacharide," and insert -- Lipopolysaccharide, --, therefor.

On title page 6, in item (56), in column 2, under "Other Publications", line 44, delete "Allergoloy" and insert -- Allergology --, therefor.

Signed and Sealed this
Third Day of February, 2015

Michelle K. Lee
*Deputy Director of the United States Patent and Trademark Office*

On title page 6, in item (56), in column 2, under "Other Publications", line 46, delete "Alloe" and insert -- Aloe --, therefor.

On title page 6, in item (56), in column 2, under "Other Publications", line 64, delete "Macacque:" and insert -- Macaque: --, therefor.

On title page 7, in item (56), in column 2, under "Other Publications", line 3, before "CAMP" delete "T".

On title page 7, in item (56), in column 2, under "Other Publications", line 32, delete "Sury" and insert -- Surv --, therefor.

On title page 7, in item (56), in column 2, under "Other Publications", line 44, after "Sclerosis" insert -- Symptoms --.

In the Specification

In column 3, line 53, delete "dihydrotesterone" and insert -- dihydrotestosterone --, therefor.

In column 5, line 30, delete "a" and insert -- α --, therefor.

In column 5, line 31, delete "13" and insert -- β --, therefor.

In column 6, line 58, delete "a" and insert -- α --, therefor.

In column 7, line 33, delete "the a" and insert -- a --, therefor.

In column 7, line 49, delete "thereof" and insert -- thereof. --, therefor.

In column 7, line 57, delete "composition" and insert -- composition. --, therefor.

In column 9, line 11, delete "thereof" and insert -- thereof. --, therefor.

In column 14, line 19, delete "the a" and insert -- a --, therefor.

In column 20, line 21, delete "mange" and insert -- manage --, therefor.

In column 21, line 7, delete "betain," and insert -- betaine, --, therefor.

In column 21, line 57, delete "Ompound" and insert -- Compound --, therefor.

In column 24, line 49, delete "N-methylpyrrolidone" and insert -- N-methyl pyrrolidone --, therefor.

In column 24, line 51, delete "mange" and insert -- manage --, therefor.

In column 27, line 11, delete "weight" and insert -- weight. --, therefor.

In column 27, line 43, delete "aminomethylpropanol," and insert -- aminomethyl propanol, --, therefor.